US007811272B2

(12) United States Patent  
Lindsay et al.

(10) Patent No.: US 7,811,272 B2
(45) Date of Patent: Oct. 12, 2010

(54) NANOFABRICATED GECKO-LIKE FASTENERS WITH ADHESIVE HAIRS FOR DISPOSABLE ABSORBENT ARTICLES

(75) Inventors: Jeffrey Dean Lindsay, Appleton, WI (US); Fung-Jou Chen, Appleton, WI (US); Lisha Yu, Appleton, WI (US); Nadezhda Efremova, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1076 days.

(21) Appl. No.: 10/747,923

(22) Filed: Dec. 29, 2003

(65) Prior Publication Data

US 2005/0148984 A1    Jul. 7, 2005

(51) Int. Cl.
A61F 13/15 (2006.01)
A61F 13/20 (2006.01)
B32B 5/00 (2006.01)
B32B 7/00 (2006.01)

(52) U.S. Cl. .................. 604/389; 604/386; 428/98; 428/99; 428/100

(58) Field of Classification Search ............ 24/442; 428/99, 141, 100; 604/386–391, 358; 977/773, 977/961

See application file for complete search history.

(56) References Cited

U.S. PATENT DOCUMENTS

| 2,787,241 | A |   | 4/1957 | Kelley |
| 3,397,697 | A |   | 8/1968 | Rickard |
| 4,285,343 | A |   | 8/1981 | Mcnair |
| 4,299,223 | A | * | 11/1981 | Cronkrite ............... 604/390 |
| 4,323,069 | A | * | 4/1982 | Ahr et al. ............... 604/378 |
| 4,556,146 | A |   | 12/1985 | Swanson et al. |
| 4,585,450 | A | * | 4/1986 | Rosch et al. ............ 604/390 |
| 4,589,876 | A |   | 5/1986 | Van Tilburg |
| 4,593,418 | A | * | 6/1986 | Simon .................... 2/275 |
| 4,608,047 | A |   | 8/1986 | Mattingly |
| 4,645,501 | A | * | 2/1987 | Teed ...................... 604/390 |
| 4,687,478 | A |   | 8/1987 | Van Tillburg |
| 4,716,067 | A | * | 12/1987 | Moji et al. ............. 428/117 |
| 4,753,649 | A |   | 6/1988 | Pazdernik |

(Continued)

FOREIGN PATENT DOCUMENTS

EP    0 923 902 A2    6/1999

(Continued)

OTHER PUBLICATIONS

Borchardt, John, "Nanotechnology Providing new Composites", Reinforced Plastics, vol. 47, No. 10, Nov. 2003, pp. 36-39(4).*

(Continued)

Primary Examiner—Melanie J Hand
(74) Attorney, Agent, or Firm—Bryan R. Rosiejka

(57) ABSTRACT

A disposable absorbent article has a nanofabricated attachment means having adhesive hairs disposed on a substrate wherein the hairs are effective to adhesively engage an opposing surface having a polymeric film or a fibrous web. In another embodiment, the absorbent article has a gecko-like fastener including a substrate and a plurality of adhesive hairs arising from the substrate having a base section, midsection, and top section, a height of about 0.5 microns to about 8 millimeters, and a diameter greater than about 0.05 microns.

45 Claims, 12 Drawing Sheets

U.S. PATENT DOCUMENTS

| | | | |
|---|---|---|---|
| 4,834,739 A | | 5/1989 | Linker, III et al. |
| 4,917,697 A | | 4/1990 | Osborn, III et al. |
| 5,011,480 A | | 4/1991 | Gossens et al. |
| 5,279,604 A | * | 1/1994 | Robertson et al. ............ 604/389 |
| 5,354,597 A | * | 10/1994 | Capik et al. .................. 428/152 |
| 5,399,219 A | | 3/1995 | Roessler et al. |
| 5,558,660 A | * | 9/1996 | Dreier .................... 604/385.19 |
| 5,681,303 A | | 10/1997 | Mills et al. |
| 5,683,377 A | * | 11/1997 | Mizutani ..................... 604/390 |
| 5,766,387 A | | 6/1998 | Wolf et al. |
| 5,766,389 A | | 6/1998 | Brandon et al. |
| 5,772,648 A | * | 6/1998 | Osborn et al. .......... 604/385.04 |
| 5,858,515 A | | 1/1999 | Stokes et al. |
| 6,127,018 A | * | 10/2000 | Akeno et al. ................. 428/100 |
| 6,350,517 B1 | * | 2/2002 | Wu ............................. 428/354 |
| 6,501,002 B1 | | 12/2002 | Roe et al. |
| 6,561,354 B1 | | 5/2003 | Fereshtehkhou et al. |
| 6,562,167 B2 | | 5/2003 | Coenen et al. |
| 6,726,386 B1 | * | 4/2004 | Gruenbacher et al. .......... 401/7 |
| 6,872,439 B2 | * | 3/2005 | Fearing et al. ................ 428/99 |
| 2001/0032568 A1 | * | 10/2001 | Schutt .................... 106/287.11 |
| 2002/0138064 A1 | * | 9/2002 | Datta et al. .................. 604/391 |
| 2003/0044569 A1 | * | 3/2003 | Kacher et al. ................ 428/100 |
| 2003/0100880 A1 | * | 5/2003 | Magee et al. ............... 604/389 |
| 2003/0124312 A1 | | 7/2003 | Autumn |
| 2003/0208888 A1 | | 11/2003 | Fearing et al. |

FOREIGN PATENT DOCUMENTS

| | | | |
|---|---|---|---|
| WO | WO 91/18574 A1 | | 12/1991 |
| WO | WO 98/52458 A1 | | 11/1998 |
| WO | WO 01/41622 A2 | | 6/2001 |
| WO | WO 01/49776 A2 | | 7/2001 |
| WO | WO 01/49776 A3 | * | 7/2001 |
| WO | WO 0149776 A3 | * | 7/2001 |
| WO | WO 03/000104 A1 | | 1/2003 |
| WO | WO 03095190 A1 | * | 11/2003 |

OTHER PUBLICATIONS

Borchardt, John, "Nanotechnology Providing new Composites", Reinforced Plastics, vol. 47, No. 10, Nov. 2003, pp. 36-39(4).*

Geim, A.K. et al., "Microfabricated Adhesive Mimicking Gecko Foot-Hair," Nature Materials, vol. 2, Jul. 2003, pp. 461-463, available at Internet web page "http://www.nature.com/cgi- taflDynaPage.taf?file=Inmat/journallv21n71fullInmat917.html", Jun. 1, 2003.*

Schmid, H. and B. Michael, "Siloxane Polymers for High-Resolution, High-Accuracy Soft Lithography," Macromolecules, vol. 33, Apr. 2000, p. 3042-3049.

Sekine, M., "Dielectric Film Etching in Semiconductor Device Manufacturing Development of SiO2 Etching and the Next Generation Plasma Reactor," Appl. Surf. Science, 192, 2002, pp. 270-298.

Sitti, Metin and Ronald S. Fearing, "Nanomolding Based Fabrication of Synthetic Gecko Foot-Hairs," Second IEEE Conference on Nanotechnology, Washington, D.C., Aug. 26-28, 2002, 4 pages, available at Internet web page http://robotics.eecs.berkeley.edu/~ronf/PAPERS/nano_02.pdf.

Xia, Younan and G. Whitesides, "Soft Lithography," Angewandte Chemie: International Edition, vol. 37, No. 5, Mar. 1998, pp. 551-575.

Yin, Sandra, interview, "Kellar Autumn: Lewis & Clark College Biologist Shows How the Gecko Gets Its Grip," American Demographics, Futurespeak: Science's Potential to Create New Markets, Dec. 2002/Jan. 2003, p. 52.

Zimmer, Carl, "Get a Grip," Natural History, Jul./Aug. 2000, 1 page, available at Internet web page "http://www.carlzimmer.com/articles_2000_2.html".

"Gecko's Amazing Sticky Feet," BBC News Online, Jun. 7, 2000, 3 pages, available at Internet web page "http://news.bbc.co.uk/hi/english/sci/tech/newsid_78100/781611.stm".

"Gecko's Toes Provide Model for Super-Adhesive Space Tape," HowStuffWorks (http://www.howstuffworks.com), Internet web page "http://www.howstuffworks.com/news-item21.htm", HowStuffWorks, Inc., 2003, 2 pages.

Autumn, Kellar and Robert J. Full, Gecko Images, available at Internet web page, "http://www.lclark.edu/~autumn/private/u38j47a0t/images.html", 2000, 1 page.

Autumn, Kellar, et al. "Adhesive Force of a Single Gecko Foot-Hair," Nature, vol. 405, Jun. 8, 2000, pp. 681-685.

Autumn, K. et al., "Evidence for van der Weals Adhesion in Gecko Setae," Proceedings of the National Academy of Sciences of the United States of America, vol. 99, No. 19, Sep. 17, 2002, pp. 12,252-12,256.

Geim, A.K. et al., "Microfabricated Adhesive Mimicking Gecko Foot-Hair," Nature Materials, vol. 2, Jul. 2003, pp. 461-463, available at Internet web page "http://www.nature.com/cgi-taf/DynaPage.taf-?file=/nmat/journal/v2/n7/full/nmat917.html", Jun. 1, 2003.

Janra, "Gecko Feet In-hair-ently Sticky", Oct 18, 2002, available at www.kuro5hin.org/print/2002/10/18/03840/816.

Liu, Gang-Yu et al., "Nanofabrication of Self-Assembled Monolayers Using Scanning Probe Lithography," *Accounts of Chemical Research*, vol. 33, No. 7, 2000, p. 457-466.

Menzel, Peter and Faith D'Aluisio, "Biobotics: Can Man Mimic Organic Life-Forms With Machinery?" Discover, Sep. 2000, pp. 86-93.

Piner, R.D. et al., "'Dip-Pen' Nanolithography," *Science,* vol. 283, Issue 5402, Jan. 29, 1999, p. 661, 5 pages.

Powell, Kendall, "Gecko Glue Around the Corner," Nature—Science Update, Aug. 28, 2002, 2 pages, available at Internet web page "http://www.nature.com/nsu/020826/020826-2.html".

Schmelmer, U. et al., "Surface-Initiated Polymerization on Self-Assembled Monolayers: Amplification of Patterns on the Micrometer and Nanometer Scale," *Angewandte Chemie: International Edition,* vol. 42, No. 5, Feb. 2003, pp. 559-563.

* cited by examiner

NANOFABRICATED GECKO-LIKE FASTENERS WITH ADHESIVE HAIRS FOR DISPOSABLE ABSORBENT ARTICLES

BACKGROUND

Traditionally, adhesive materials comprise wet glue-like substances that are sticky to the touch and tend to leave a residue when removed. Additionally, these substances tend to be limited in use. For example, their efficacy may be substantially reduced in water, in vacuums, on certain plastics, on certain fabrics, etc. A hook-and-loop type fastener may overcome some of the deficiencies noted in traditional glue-like adhesive materials; however, a dual surface (i.e., two separate surfaces designed to engage one another) is required to enable such a fastener. A magnet may also overcome some of the deficiencies noted in traditional glue-like adhesive materials; however, magnets are limited to ferrous materials. Such difficulties are particularly noted when fastening a disposable absorbent article.

Geckos have a remarkable ability to climb and adhere to surfaces of many different kinds, including smooth hydrophobic and hydrophilic surfaces. Examination of gecko feet reveals that numerous minute hairs, called setae, are the agents of this adhesion. These gecko setae, with diameters in the range of 0.2 to 0.5 microns, are adapted to conform well to the microscopic structure of whatever surface the geckos wish to traverse. As the setae contact the surface, an attraction between the setae and the opposing surface can allow the setae to adhere with forces in the order of 100 nanoNewtons (nN) each. At the same time, the setae can be readily separated from an opposing surface by what is surmised to be the curling of the gecko's toes to peel the setae away. The movement of the gecko allows the setae to repeatedly be adhered to and removed from opposing surfaces. Principles of gecko adhesion are discussed in more detail by Kelly Autumn et al., "Evidence for van der Waals Adhesion in Gecko Setae," *Proceedings of the National Academy of Sciences of the United States of America*, Vol. 99, No. 19, pp. 12,252-12,256 (Sep. 17, 2002), and by Robert J. Full et al., "Adhesive Microstructure and Method of Forming the Same," WO 01/49776, published Jul. 12, 2001, both of which are incorporated by reference in their entireties. Principles for construction of biomimetic gecko-like adhesives are also disclosed in U.S. patent application Ser. No. 10/197,763, filed Jul. 18, 2002 by Fearing et al. and in U.S. patent application Ser. No. 10/039,574, filed Jan. 2, 2002 by Autumn et al., both of which are herein incorporated by reference.

It is therefore desirable to obtain a fastening means for a disposable absorbent article that is dry in nature. It is further desirable that such a fastener would be sticky only when desired. It is further desirable that such a fastener would not leave a residue when removed. It is further desirable that such a fastener would stick to most surfaces. It is still further desirable that such a fastener would require only a single surface for adhesion.

SUMMARY

In general, a disposable absorbent article according to one example of the present invention comprises at least one nanofabricated gecko-like fastening means. The fastening means comprises hairs that have a base section, a midsection, and a top section. The hairs have a height of about 0.5 microns to about 8 millimeters and a diameter of about 0.05 microns, and in one example, can have a packing density of at least 500 hairs per square meter.

In one example of the present invention, the hairs are spaced apart by a first distance of about 1 micron to about 1000 microns. The hairs may be further spaced apart by a second distance of about 1 micron to about 1000 microns. The ratio of the first distance to the diameter of the hairs can be about 3 to about 100, and the ratio of the second distance to the diameter of the hairs can also be about 3 to about 100. Additionally, the ratio of the height to the diameter of said hairs can be about 2 to about 1000.

In one example of the present invention, at least one of the hairs is perpendicular to the plane of the substrate. In another example, at least one of the hairs can be oriented at an angle between 0 and 90° to the plane of said substrate. In yet another example, at least one of the hairs is axisymmetric, and additionally can have an end portion that is flattened.

In one example of the present invention, at least one of the hairs is hollow. In other examples, at least one of the hairs comprises hollow materials, such as microspheres, carbon nanotubes, zeolites. In still other examples, the hairs comprise molecules with hollow chambers, such as cyclodextrins, polyhedral oligomeric silsequioxanes, crown ethers, and the like.

In further examples of the present invention, the substrate of the fastening means can be either a single layer or have multiple layers. The substrate can also comprise various materials. For example, the substrate can be a film, which further can be apertured or embossed. The film can also be a fibrous web. Such a web can be liquid impervious and can comprise a number of materials, such as a meltblown or an activated carbon fabric. In general, the substrate can be, inter alia, creped, embossed, apertured, or coated on at least one side. The substrate can also contain regions of elasticity or stretchability. Furthermore, the thickness of the substrate can be either uniform or non-uniform.

In additional examples of the present invention, the fastener can be adapted for fastening the article to itself, to another object, or for joining two or more components of the article. The fastener may also comprise a protecting material to prevent adhesion until desired.

The individual setae may be adapted to each provide an adhesive force, on the average, as measured against a clean, flat silicon wafer, of about 10 nanoNewtons (nN) or greater, specifically about 30 nN or greater, more specifically about 50 nN or greater, and most specifically about 70 nN or greater, with an exemplary range of from about 20 nN to about 2,000 nN, or from about 40 nN to about 800 nN.

In general, a method according to one example of the present invention for fastening a disposable absorbent article generally comprises a gecko-like fastener comprising adhesive hairs rising from a substrate and having a height of about 0.5 microns to about 8 millimeters and a diameter greater than about 0.05 microns, and an opposing surface that can comprise synthetic or natural material, and can comprise hydrophilic or hydrophobic properties. Additionally, the opposing surface may be smooth or textured, substantially liquid pervious or liquid impervious, substantially flexible or inflexible, porous or non-porous, and flexible or inflexible.

In some examples of the present invention, the gecko-like adhesive hairs can be used in refastenable absorbent articles to replace hook and loop materials to provide a soft, flexible fastening means that is less likely to chaff or irritate the skin than conventional hook and loop materials.

Other features of the invention will be in part apparent and in part pointed out hereinafter.

DEFINITIONS

As used herein, the term "gecko" means any of numerous small, harmless, chiefly tropical and nocturnal insectivorous lizards (family Gekkonidae)

As used herein, the term "gecko-like adhesive" refers to an adhesive material comprising minute hairs rising from a substrate capable of conforming to and adhering to an opposing surface. Further description of the nature of gecko-like adhesives are set forth herein.

As used herein, the term "nanofabricated" refers to the production of materials with functional elements typically at a submicron scale, and can refer to processes such as nanolithography, ion etching, laser nanomachining, nanoimprinting, molecular self-assembly, electron-beam lithography, and other processes known in the art of nanotechnology.

As used herein, the term "setae" (the plural of "seta," the Latin word for bristle) refers to short hairs or hairlike structures such as those found on the toes of geckos, and other man-made structures that mimic gecko hairs or achieve similar functionality.

As used herein, "terminating elements" are structures that extend from the end of the shafts of setae, generally being finer that the shaft of the setae. A naturally occurring example of terminating elements are the fine spatulae that extend from the setae of gecko toes. A single seta may have a plurality of terminating elements extending therefrom, such as from 1 to 20 terminating elements or two or more terminating elements.

As used herein, the term "axisymmetric means symmetric in respect to an axis.

DETAILED DESCRIPTION

Figure 1:
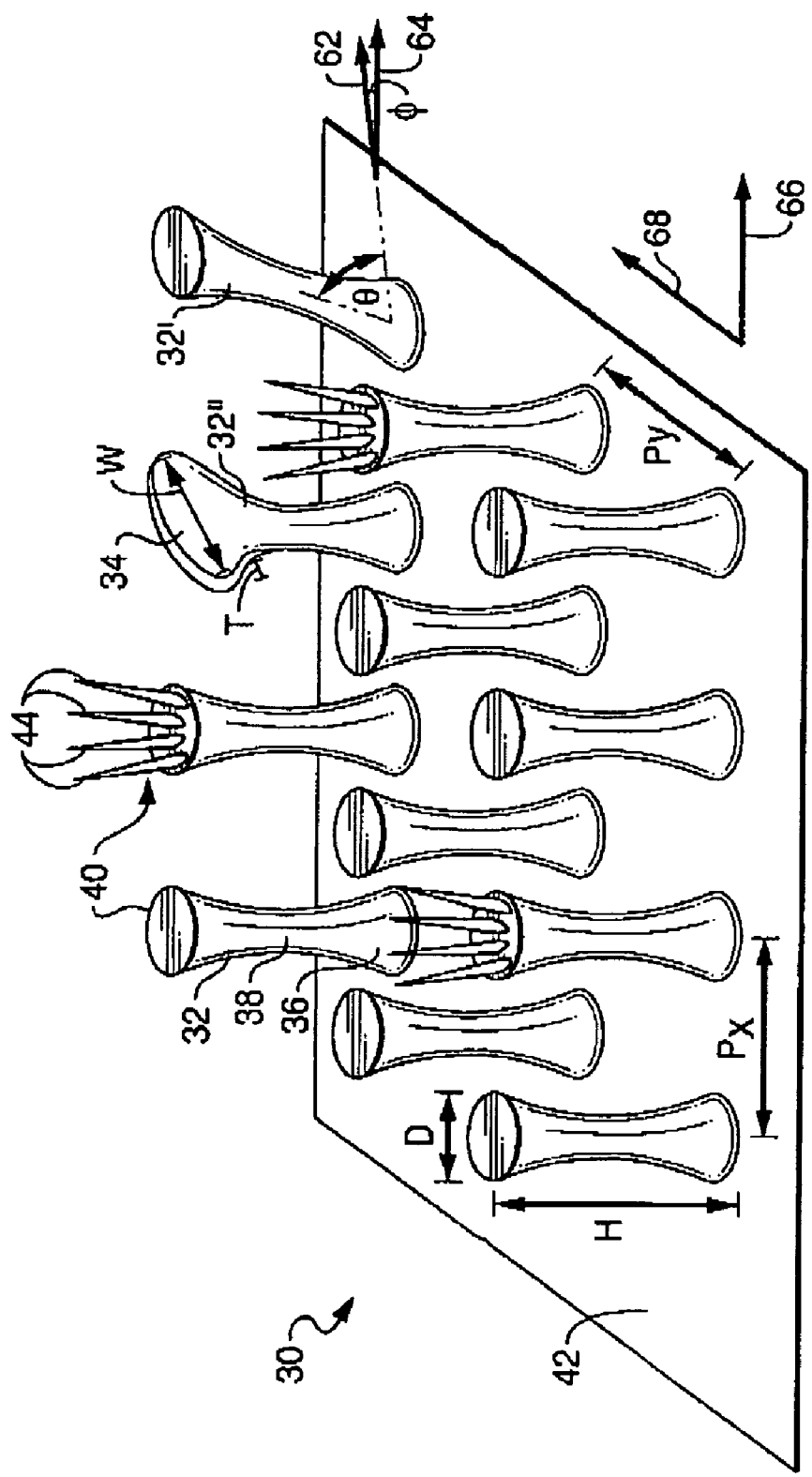
FIG. 1 is a top view of an enlarged section of gecko-like adhesive material.

With respect to FIG. 1, the present invention comprises a section of gecko-like adhesive material 30 adapted for use as a fastener in an absorbent article (not shown), the adhesive material 30 comprising a substrate 42, a plurality of adhesive hairs 32 rising from the substrate 42, the adhesive hairs 32 each having a base section 36, a midsection 38, and a top section 40, the top section 40 optionally terminating in a plurality of fine terminating elements 44 which can mimic the spatulae of gecko setae or otherwise provide for enhanced conforming and contact area between the adhesive hairs 32 and a contact surface (not shown). Each hair has a height H and a diameter D (or range of diameters throughout a given hair). The height H may be from about 0.5 microns to about 8 mm, such as from about 2 microns to about 1000 microns, more specifically from about 2 microns to about 500 microns, more specifically still from about 4 microns to about 200 microns, and most specifically from about 5 microns to about 100 microns. The diameter D may be greater than about 0.05 microns or from about 0.1 microns to about 50 microns, such as from about 0.1 microns to about 10 microns, more specifically from about 0.2 microns to about 5 microns, more specifically still from about 0.2 microns to about 2 microns, and most specifically from about 0.3 microns to about 1 micron, or alternatively less than about 5 microns or less than about 3 microns. The hairs 32 may be spaced apart in a pattern, with successive hairs 32 in a first direction 66 (e.g., the machine direction 64) spaced apart by a first characteristic distance $P_x$, and optionally with successive hairs 32 in a second direction 68 (e.g., the cross direction orthogonal to the machine direction 64, or another in-plane direction) spaced apart by a second characteristic distance $P_y$. The values of $P_x$ and $P_y$ may independently be greater than about 1 micron, such as from about 1 micron to about 1000 microns, specifically from about 1 micron to about 100 microns, more specifically from about 1 microns to about 40 microns, and most specifically from about 2 microns to about 30 microns. Alternatively, the ratio of either $P_x$ or $P_y$ to the diameter D may be about 3 or greater, such as any of the following: about 5 or greater, about 10 or greater, about 20 or greater, about 30 or greater, about 50 or greater, about 100 or greater, from about 5 to about 100, from about 10 to about 70, and from about 20 to about 50. The ratio of the height H to the diameter D may be any of the following: about 2 or greater, about 5 or greater, about 10 or greater, about 20 or greater, about 30 or greater, about 40 or greater, about 50 or greater, about 100 or greater, from about 3 to about 1000, from about 10 to about 200, from about 5 to about 100, and from about 5 to about 50.

Though the adhesive hairs 32 are shown as perpendicular to the plane of the substrate 42, each adhesive hair 32 may be individually or collectively oriented at an angle θ relative to the plane of the substrate 42 (or relative to the horizontal plane), as is the case for the adhesive hair labeled 32'. Such an adhesive hair 32' is said to be leaning at vertical angle θ, and leans in a particular leaning direction 62 relative to the machine direction 64 (or other predetermined reference orientation) of the adhesive material 30, with an in-plane angle φ between the leaning direction 62 and the machine direction 64.

Though not shown, there may be two or more subsets of the adhesive hairs having different properties, such as a first subset at a first vertical angle and a second subset at a second vertical angle. The two or more subsets may be randomly distributed or dispersed in a pattern such as a staggered grid array or two discrete clusters.

While the adhesive hairs 32 as shown are generally axisymmetric, they can be made in any desirable shape, including shapes such as that for the adhesive hair 32" which has an axisymmetric base 36 and a flattened end portion 34 with a width W and a thickness T. The ratio of W to T may be about 2 or greater, such as about 5 or greater, about 10 or greater, or about 20 or greater, specifically from about 3 to about 25, more specifically from about 5 to about 25, and most specifically from about 10 to about 25. The flattened end portion 34 may occupy about 5% or more of the height H of the adhesive hair 32', such as about 10% or more, about 20% or more, or about 40% or more, specifically from about 10% to 80%, more specifically from about 20% to about 60%, and most specifically from about 20% to about 40% of the height H of the adhesive hair. There may be two or more sets of adhesive hairs 32 differing in any of these properties and distributed randomly or in one or more patterns.

The adhesive hairs 32 also may be hollow (not shown), such as hollow tubes, or may comprise hollow materials such as hollow microspheres, carbon nanotubes, zeolites, and the like, or may comprise molecules with hollow chambers such as cyclodextrins or polyhedral oligomeric silsequioxanes (POSS) macromers. POSS materials are cage-like compounds that represent the smallest possible unit of silica. Reactive groups on the molecules can allow them to bind to each other or to other organic compounds. The particle diameter of the POSS molecules is in the range 0.7-30 Å, on average much smaller than the diameter of typical colloidal silica particles. POSS materials are available from Hybrid Plastics, Fountain Valley, Calif.

The substrate 42 can comprise a single layer or multiple layers of material. It can be a film, an apertured film, a fibrous web, a liquid pervious web such as a meltblown web, an activated carbon fabric, and the like, or a composite structure comprising one or more such materials. The thickness of the substrate may be uniform or nonuniform, and may have a repeating pattern (not shown) of thickness variations such as a rectangular grid or series of lines having 10% or greater thickness than the mean thickness of the substrate. The substrate 42 may be a film or web that has been creped, embossed, apertured, coated on one or both sides with a hydrophobic or hydrophilic agent or a metal oxide such as titanium dioxide, treated with a UV absorbing material, thermally treated to cause shrinkage, and the like.

In one embodiment, the substrate 42 comprises regions of elastic material, and optionally may be substantially elastic and homogeneous, or contain discrete elastic regions separated by or surrounded by less elastic or inelastic regions.

The adhesive material 30 itself can be stretchable or comprise elastic regions. Further, the attachment surface (not shown) to which the adhesive material will be attached may be elastic, inelastic, or comprise regions of both elastic and inelastic material.

The adhesive material 30 can be adapted for fastening an absorbent article to itself or to another object such as undergarments (not shown), an article of clothing, skin, linens, blankets, bedcovers, plastic components, biosensors, or for joining two or more components of the absorbent article. The adhesive material 30 may function in an absorbent article (not shown) as part of a side seam, as a replacement for any known adhesive fastening system or mechanical fastening system such as hook and loop attachment means, and the like. The absorbent article may comprise a combination of the adhesive material 30 as well as other known adhesive or mechanical fastener systems.

Suitable articles which can comprise an adhesive material 30 of the present invention include diapers, disposable training pants, prefastened absorbent articles such as those that can serve as both diapers or training pants, incontinence articles, sanitary napkins, ostomy bags, disposable garments, disposable surgical gowns, face masks, inserts for absorbent articles, shoe inserts, antiperspirant patches, breast pads, helmet liners, wound dressings, sterile wrap, covers for automobiles, disposable ground covers, etc., as well as the materials and articles disclosed in WO 01/49776.

Figure 2A:
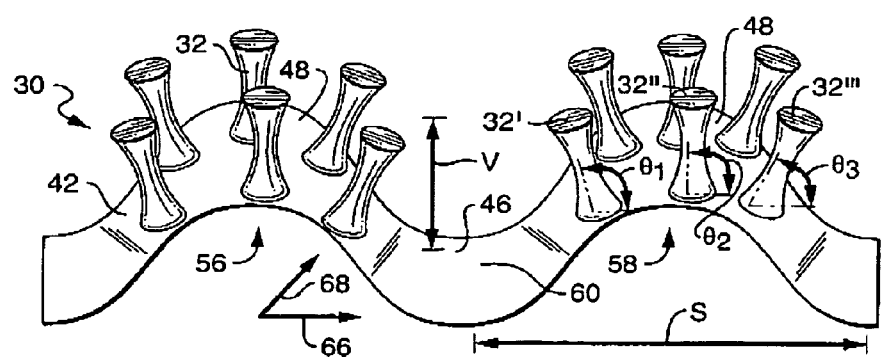
FIG. 2A is a top view of an enlarged section of gecko-like adhesive material depicting peaks and valleys with hairs selectively located on the peaks.

The adhesive material 30 can be used to join an article such as an absorbent article or a component thereof to any opposing surface (not shown). The opposing surface can be hydrophilic or hydrophobic or comprising alternating or mixed regions of both hydrophilicity or hydrophobicity. The opposing surface may comprise a synthetic material such as a polymer (e.g., polyolefins, polyesters, polyamides, polyimides, rayon, styrenic block copolymers (SBC), isoprene or butadiene mid-block polymers, styrene isoprene styrene (SIS) polymers, phenolic polymers, neoprene, silicone polymers, fluoropolymers, and the like) or may comprise a natural material such as skin, leather, hair, mammalian nails, organic membranes, cellulose, keratin, chitin, silk, wood, plant matter, and the like, or derivatives and combinations thereof. The opposing surface may also comprise glass, ceramics, metals, composite materials such as fiber-resin composites, activated carbon and activated carbon fabrics, and the like. The opposing surface may be in the form of a fibrous web, a film, an apertured web or film, a foam, and the like, and may include packaging materials, clothing, disposable articles, household items, and the like. The opposing surface may comprise a smooth or textured surface, and may be substantially liquid impervious or liquid pervious, substantially flexible or inflexible, substantially elastomeric or inelastic, substantially porous or having a porosity less than 10% or less than about 1%, and may comprise a combination of any of the aforementioned materials or material properties, such as a laminate of natural and synthetic materials, a mixture of porous and nonporous material joined together by an adhesive material, or a film with added regions of a foam such as high internal phase emulsion (HIPE) foams, FIG. 2A depicts another embodiment of an adhesive material 30 wherein the substrate 42 has a three-dimensional topography characterized by a series of peaks 48 and valleys 46, with a characteristic valley depth V (elevation difference between the peaks and the valleys), spaced apart with a characteristic spacing S between successive valleys. Here the peaks and valleys alternate in a first direction 66 (which may be the machine direction or another direction). As shown, the adhesive hairs 32 are grouped together in a plurality of groups, such as a first group 56 and a second group 58, with a substantially hair free region 60 disposed between the hair-containing groups 56, 58.

Due to the three-dimensional topography of the substrate 42, the individual hairs 32 may be at a variety of angles relative to the horizontal plane, even when the hairs 32 rise at a constant angle from the plane of the substrate in the vicinity of the hairs 32 (here the hairs are substantially perpendicular to the substrate). Thus, relative to a horizontal first direction 66 for the adhesive material 30 as lies substantially horizontally, some hairs 32' may lie at a first angle $\theta_1$ relative to a horizontal vector in the first direction 66, while other hairs 32" and 32''' lie at angles of $\theta_2$ and $\theta_3$, respectively, relative to the horizontal vector in the first direction 66. Further, as depicted, the groups comprising adhesive hairs may be selectively disposed on the peaks 48 of the substrate, or alternatively may be selectively disposed on valleys 46 of the substrate (not shown). Alternatively, the groups 56, 58 of adhesive hairs 32 may be spaced apart at a spacing other than the characteristic spacing S between successive valleys 46, such that some groups of hairs 32 fall on the peaks 48 and others fall on the valleys. In another embodiment, the adhesive hairs 32 are disposed substantially uniformly along the adhesive material 30, or, in another embodiment, the hairs 32 are disposed substantially randomly along the adhesive material 30.

Figure 2B:
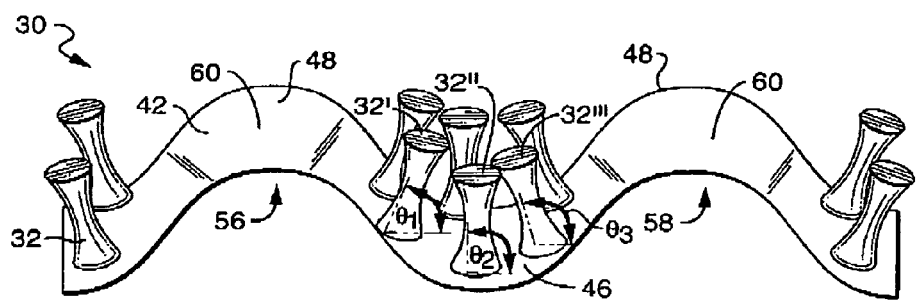
FIG. 2B is a top view of an enlarged section of gecko-like adhesive material depicting peaks and valleys with adhesive hairs selectively located in the valleys.

FIG. 2B shows an adhesive material 30 similar to that of FIG. 2A, except that the adhesive hairs 32 are selectively located in the valleys 46, and the peaks 48 are generally part of the hair free regions 60. In this embodiment, the adhesive hairs 32 may be protected from contamination with other materials until pressed into contact with an opposing surface (not shown). Stretching of the adhesive material 30 may also be applied to raise the valleys 46 with respect to the peaks 48, thus making the adhesive hairs 32 more easily accessible for adhesion to opposing surfaces.

Alternatively, the adhesive hairs of FIGS. 1, 2A, and 2B may further be protected with a removable cover (not shown) to protect them from premature adhesion or contamination, similar in principle to a silicone-coated release paper that is commonly placed over pressure-sensitive adhesive regions in absorbent articles to prevent premature adhesion. The removable cover may be a paper strip coated with a silicon, a fluoropolymer, a wax, or other material capable, or may be a film or other web.

Figure 3:
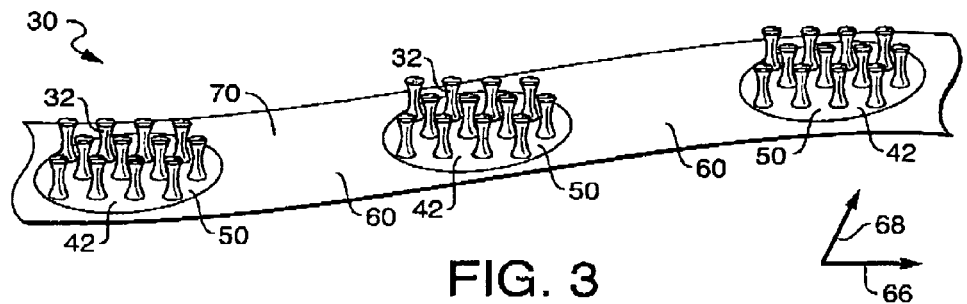
FIG. 3 is a top view of an enlarged section of gecko-like adhesive material depicting spaced apart, discrete patches of adhesive hairs.

FIG. 3 illustrates another embodiment of an adhesive material 30 of the present invention, here shown as a tape-like length of a thin, flexible base layer 70 onto which has been disposed spaced apart, discrete patches 50 comprising a substrate 42 supporting gecko-like adhesive hairs 32, with substantially adhesive-hair-free regions 60 of the base layer separating the patches 50. The patches 50 are spaced apart in a first direction 66 of the base layer 70, which may be the machine direction or may be the direction in which the base layer 70 is most extensible. The substrate may be elastomeric, or may be a creped or foreshortened material which can be stretched in one or more directions, but does not necessarily retract substantially when the extensional force applied to the base layer 70 is relaxed. If the base layer 70 is substantially elastic, it may, for example, be extended in a direction by about 20% of its initial length upon application of a predetermined extensional force in that direction, and then, upon removal of the extensional force, retract to a length no greater than about 10% longer than its initial length.

The patches 50 may be thin films such as a polymer film having a thickness less than 50 microns or less than 30 microns, or may have greater thickness (e.g., from about 0.05 to about 3 millimeters, or from about 0.1 to about 1.5 millimeters). The patches may be substantially inelastic or may be elastic, and may have a Young's modulus greater than that of the base layer 70, such as at least about 10% greater, at least about 50% greater, or at least about 100% greater than that of the base layer 70.

In general, adhesive hairs 32 mimicking gecko setae can be provided on small patches of a stretchable base layer 70 such that the patches 50 move apart when the base layer 70 is stretched. The base layer 70 material may be readily stretchable in one or more directions, and may be flat, three-dimensional, porous, non-porous, fibrous, a film, and may comprise apertures. The base layer 70 may also have a three-dimensional texture.

The adhesive material 30 may be used as an attachment means for closing an absorbent article (not shown) around the torso or a wearer, or as attachment means for joining the absorbent article to another article such as an article of clothing, or as a body adhesive for joining a portion of an absorbent article to the skin of a wearer (e.g., joining leg cuffs of a diaper or a waist cuff of a diaper to the body of the wearer for improved gasketing to reduce leakage of fluids such as urine).

Figure 4:
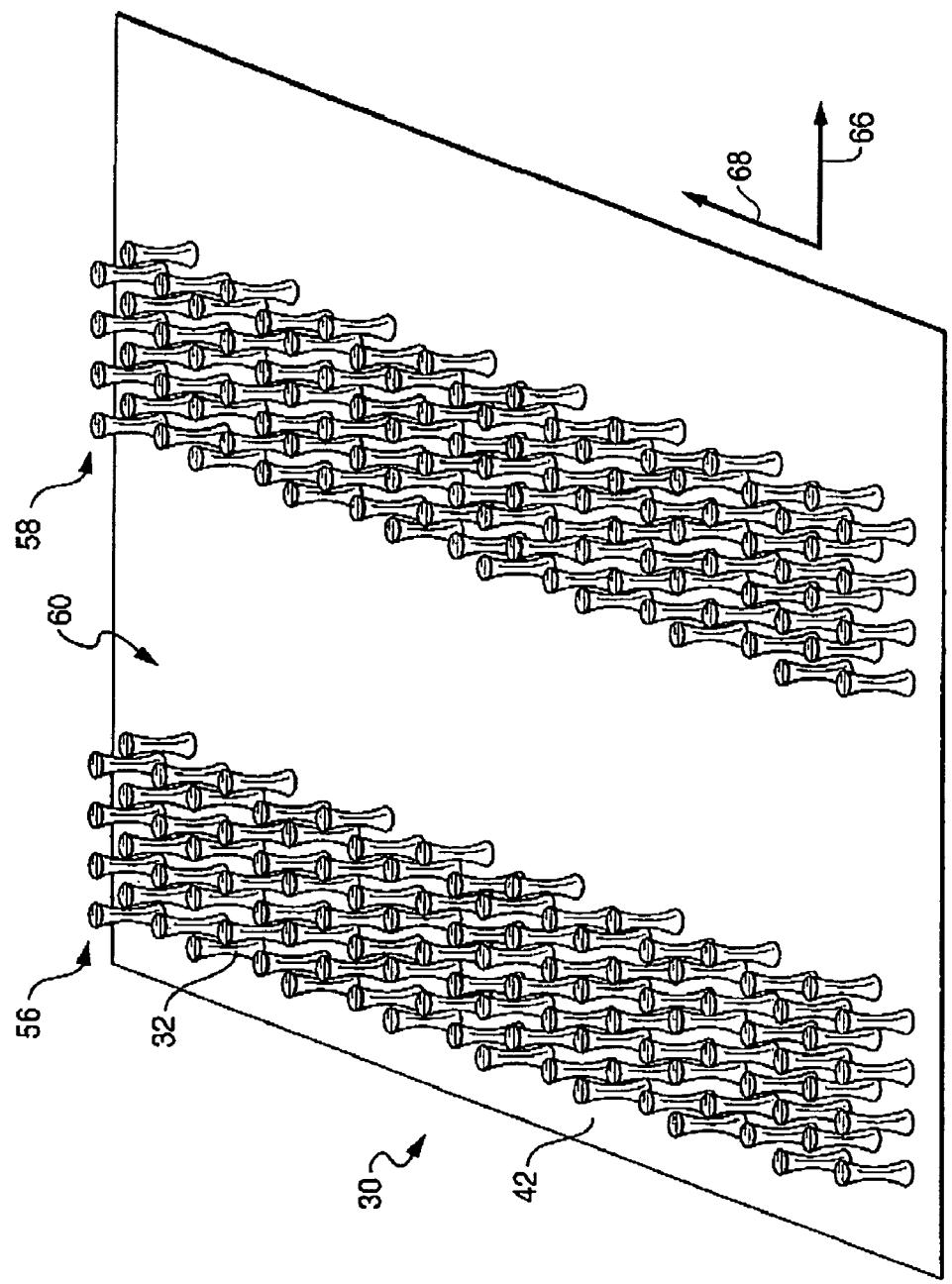
FIG. 4 is a top view of an enlarged section of gecko-like adhesive material depicting adhesive hairs disposed in distinct groups separated by adhesive-hair-free regions.

FIG. 4 depicts a section of an adhesive material 30 according to the present invention in which adhesive hairs 32 on a substrate 42 are disposed in distinct groups 56, 58 separated by adhesive-hair-free regions of the substrate 42. The hair free region 60 may have a width of about 1 micron or greater, such as about 5 microns or greater, about 10 microns or greater, or about 20 microns of greater, with exemplary ranges of from about 5 microns to about 100 microns, or from about 15 microns to about 200 microns.

Methods of Making Synthetic Gecko-Like Adhesive Materials

For the present invention, synthetic setae may be made by any known method, including lithography, nanomolding with a template or other means, etching (including ion etching), amplified self-assembled monolayers (SAMs), and the like. For example, setae can be made from hydrophobic or hydrophilic polymers. Useful polymers can include natural, synthetic, and semi-synthetic polymers or blends thereof. Exemplary polymeric materials can include keratin (e.g., β-keratin or other keratin materials and derivatives, such as those obtained from wool), polyesters, polyamides, and silicone materials. Exemplary silicone materials can include polydimethysiloxane and its derivatives and copolymers, such as diphenylsiloxane-dimethylsiloxane copolymer, Catalog No. PMM-5021 of Gelest, Inc., Morrisville, Pa., or polydimethylsiloxane aminoalkyl copolymers.

In one example, synthetic setae made from a first composition can be chemically treated to modify the surface energy of the setae, optionally without substantially modifying the topography of the setae. Thus a hydrophilic material can be chemically treated (e.g., reaction with silicone compounds) to present a relatively hydrophobic surface on at least a portion of the setae (e.g., on the tops or sides of the setae, or along one side of the setae).

In another example, a segment of gecko-like adhesive material can comprise two or more kinds of setae, such as a setae made from a hydrophobic polymer and setae made from a hydrophilic polymer. In another example, hydrophilic setae can be separated by one or more hydrophobic setae along at least one direction of the adhesive material.

In WO 01/49776, Full et al. propose several methods for producing synthetic gecko-like structures. An oxide/nitride process is disclosed, in which a recess is etched on a semiconductor substrate, after which nitride and oxide layers are deposited on the substrate. Further etching creates stresses which allow the deposited layers to be peeled off the substrate to yield a shaft structure with dimensions similar to those of setae. Roughening of the shafts by wet etching, plasma roughening, electrochemical etching, radiation, etc. can be performed, if desired, to form simulated spatulae on the simulated setae, or simulated spatulae can be adhered or deposited by other means.

Another example is provided by A. K. Geim et al. in "Microfabricated Adhesive Mimicking Gecko Foot-hair," *Nature Materials*, Vol. 2, July 2003, pp. 461-463. In initial work, Geim et al. have used an AFM (atomic force microscope) tip to produce dimples on a wax surface, which in turn has been used to make minute pyramids of a polymer. The adhesive force generated by these pyramids when in contact with another flat surface was measured at around 200 nN, similar to the adhesive forces estimated for an individual gecko hair.

Larger arrays of gecko-like hairs were made by Geim et al., applying micropatterns of elevated structures on thin, flexible polyimide films. In one example, they used electron-beam lithography and dry etching in oxygen plasma to create hairs of desired geometry. Geim et al. prepared a 5-micron-thick polyimide film (pyrometallilc dianhydride-oxidianiline polyimide, baked at 250° C.) on top of a silicon wafer. Next, by using electron beam lithography, they prepared an array of submicrometer aluminum disks. The resulting pattern of aluminum was transferred to the polyimide film by dry etching in oxygen. The oxygen plasma etching provided a large difference between etching rates of aluminum oxide and polyimide, so that several micrometers of polyimide could be removed before the aluminum mask was lost. They also applied a negative D.C. bias to the substrate, which allowed high aspect ratios to be achieved to create tall pillars. (On this point, the authors cite M. Sekine, "Dielectric Film Etching in Semiconductor Device Manufacturing Development of $SiO_2$ Etching and the Next Generation Plasma Reactor," *Appl. Surf. Science*, 192 (2002): 270-298.)

For peeling of the polyimide films from the silicon, the authors report that the film is robust when only a few microns thick, and that it can be peeled without special skills. Scotch™ Tape (3M Company, Minneapolis, Minn.) was found to be a useful and simple method of transferring the polyimide film from the silicon to a flexible substrate. Geim et al. note that transfer to another substrate would not be needed if the polyimide film itself were thicker (e.g., thicker than about 50 microns). In the present case, the films were about 5 microns thick, making handling easier if a thicker layer was attached.

The geometry of the hairs should be designed such that the hairs can conform with the generally complex contours of an opposing surface in order for enough contacts to form to create a useful cumulative force.

Geim reports that the hairs of a gecko's foot have a diameter of 0.2 to 0.5 microns, which appears to fall precisely in the range where the van der Waals interaction and capillary forces (for objects with absorbed water on the surface) become comparable. Geim et al. explored a variety of ranges for diameter (D), height (H), and periodicity (P, distance between neighboring hairs) in order to find ranges that allowed the nanofabricated polymer hairs to conform well to surfaces without clumping or falling over. The optimal geometry they recommended was with D of about 0.5 microns, P of about 1.6 microns, and H as high as they were able to achieve, about 2 microns.

Geim et al. found that a flexible, tape-like substrate instead of a solid substrate improved the adhesive force for a patch of gecko-like hairs by a factor of roughly 1,000, apparently because the flexible substrate allows the hairs to better conform to the opposing surface. A gecko-like tape made according to their methods was able to generate an adhesive force of 3 N for a 1 $cm^2$ area.

Geim et al. suggest that improved results could be obtained with other polymers such as keratin or by using more hydrophobic materials that would reduce the tendency of neighboring hairs to clump together, especially in the presence of moisture. They do no suggest silicones or silicone-treated materials, but the silicone-based hairs may offer strong and flexible materials capable of serving as adhesive hairs.

Autumn et al. have documented some of the physics of gecko adhesion in "Evidence for van der Waals Adhesion in Gecko Setae," *Proceedings of the National Academy of Sciences of the United States of America*, Vol. 99, No. 19, pp. 12,252-12,256 (Sep. 17, 2002). As part of this work, synthetic gecko-like structures were fabricated. Specifically, setae tips (spatulae) were made synthetically from two different hydrophobic materials (contact angle of 87 degrees), a silicone rubber (PDMS, polydimethylsiloxane, available from Dow Corning as HS II), and a polyester resin (TAP Plastics, Dublin, Calif.). The Young's modulus for the polymers was 0.57 MPa for the HS II and 0.85 GPa for the polyester, based on measurement of molded rectangular polymer beams of a known size. The synthetic spatulae were made with dimensions similar to those of a natural Tokay gecko spatulae (0.2 microns) using an Atomic Force Microscope (AFM)-based nanomolding technique. A flat wax surface (J. Freeman, Inc., Dorchester, Mass.) was punched with an AFM proble (Nanosensors, Wetzlar-Blankenfeld, Germany) having a conical tip with an apex radius of 10-20 nm and a height of 15 microns. The punched surface was filled with the polymer, which was then cured and peeled from the wax.

Further experimental work has been reported by M. Sitti and R. Fearing, "Nanomolding Based Fabrication of Synthetic Gecko Foot-Hairs," IEEE Conference on Nanotechnology, Aug. 26-28, 2002, Washington, D.C., available at http://robotics.eecs.berkeley.edu/~ronf/PAPERS/nano_02.pdf. The synthetic gecko hair design was based again on nanomolding a wax substrate with an AFM tip and depositing a polymer on the molded surface that was subsequently cured and peeled away. An array of silicone rubber nano-hairs was made in this process.

In WO 01/49776, Full et al. disclosed another technique that exploits an excitation source in which a sensitive material is formed on a substrate. An excitation source is used to apply excitation energy to the sensitive material. The deep-penetrating excitation alters the volume along the trajectory of excitation. The altered volume is then selectively etched away, which results in a tube. At higher densities of exposure, the remaining material becomes a random array of isolated fingers. The end of each tube is then processed to form spatulae or spatulae (terminating elements) that are attached to the tubes.

Another proposed technique relies upon the deposition of an etchable material on a substrate. Stalks are then patterned and etched from the etchable material. The etched substrate may be coated with oxide and/or nitride layers. Alternatively, polymer layers may be used as a coating. The polymer layers may be spin-cast, using materials, such as photoresist, polyimide, glass, or epoxy-based compounds. The resultant stalks are then seeded to form nanotubes, operating as spatulae.

Artificial spatulae may be formed using a glass micropipette drawn down to a narrow aperture (e.g., 500 rim) at an end. Liquid polymer is extruded through the hollow pipette and is then cured. Surface tension creates a hemispherical drop at the end of the pipette.

Materials that may be applied to the micro-pipette include low viscosity ultra violet cure epoxy, uncured silicone rubber, or polyurethane resin. The hemisphere at the end of the micro-pipette can be flattened or embossed by pressing against a polished surface. A flattened surface, such as a surface shaped like a paddle, with its larger contact area, may have better adhesive properties than a sphere.

The single spatula pipette may be used as an embossing tool to make a nano-mold by plastically deforming a material, such as molten polystyrene. A large area mold (e.g., 20 by 20 microns) may be formed by either step-and-repeat embossing or by making an array of pipettes and embossing a large pattern. For example, Full et al. suggest that an embossing tool may be applied to a polystyrene material positioned on a substrate, resulting in a patterned polystyrene surface suitable for use as a gecko-mimicking adhesive.

Alternatively, a nano-channel glass, which consists of a large bundle of hollow glass fibers, may be used. The nano-channel glass can be filled with a polymer, and then the glass can be dissolved in an acid.

Spatulae may also be formed by lithographically induced self construction. With this technique, electrostatic attraction is used to pull liquid through a mask, and thereby "sprout" spatulae.

Stalks and spatulae may also be formed from a mold using a nano-imprinting roller (see Full et al., FIGS. IIA-11B).

A 2-layer photoresist may be formed with different resist exposure sensitivities, so that the upper layer forms, for example, 100 mn square plates that are supported by much longer and thinner pedestals. Standing-wave interference patterns can be used to expose and to pattern features to fabricate large area arrays. Similar structures can be made with SiOx layers on silicon substrates by plasma etching.

Finally, according to Full et al., setae shafts may be fabricated using a sandwich of polymer layers. A polymer layer can include spin-cast polymer materials, such as photoresist, polyimide, glass, or epoxy-based compounds. A polymer layer can also include spray-deposited polymer materials, such as photoresist, polyimide, glass, or epoxy-based compounds. Alternately, a polymer layer may be an ultra-violet curable epoxy.

Based on advances in fiber generation technology, additional technologies for setae production may be proposed. A fine multicomponent fiber produced in known synthetic fiber spinning methods can be made with a complex cross-section having a plurality of regions of differing material properties. For example, a polyester and a polyolefin can be combined through suitable dies to form a fiber with a cross-section having multiple wedges (pie-shaped elements) that alternate in material composition. When the two or more polymers in a multicomponent fiber are properly selected, a treatment step can be applied to cause the segments (e.g., the wedges) of different materials to at least partially separate from one another, resulting in a fibrillated fiber having a plurality of fine elements. It is proposed that such fine structures can approach the dimensions of gecko setae and thus have the potential to serve as synthetic setae.

Multicomponent spun fiber comprising alternating wedges of a polymer (preferably having OH groups or other functional groups) may be separated by a sacrificial polymer, such that the sacrificial polymer at the end of the fiber can be removed by a solvent (a liquid, supercritical CO2, etc.) to result in fine filaments that fan out at the end of a fiber, like the hairs of a gecko. The end of the fiber, prior to removal of the sacrificial polymer, could be cut with a knife or laser or other means to deform and flatten the individual fibrils-to-be to simulate the flattened shape at the ends of gecko spatulae, which possibly provide additional surface area for good contact.

Amplified self-assembled monolayers, and particularly the use of ordered self-assembled monolayers as initiator systems for surface-initiated polymerization (SIP) for production of sub-micron structures is described by U. Schmelmer et al., "Surface-Initiated Polymerization on Self-Assembled Monolayers: Amplification of Patterns on the Micrometer and Nanometer Scale," *Angewandte Chemie*, Vol. 42, No. 5, 2003, pp. 559-563, herein incorporated by reference in its entirety. Preparation of SAMs to establish a desired pattern can be done by any known method, such as microcontact printing (see, for example, H. Schmid and B. Michael, *Macromolecules*, Vol. 33, 2000, p. 3042, and Y. Xia and G. Whitesides, *Angedwandte Chemie. Int. Ed.*, Vol. 37, 1998, p. 550), dip-pen nanolithography (R. D. Piner et al., *Science*, Vol. 283, 1999, p. 661), nanografting or nanoshaving (see G. Y. Liu et al., *Acc. Chem. Res*. Vol. 33, 2000, p. 457), and the like.

As described in the aforementioned article of U. Schmelmer et al., the deposition of functionalized SAMs in a predetermined pattern followed by surface-initiated polymerization can create controlled amplified structures (e.g., polymer brush layers) with desired topography and chemical properties. Such an approach was demonstrated, for example, by using contact printing of SAMs of ω-functionalized alkane thiols, passivation of uncovered areas by inert n-alkyl thiols, and subsequent surface initiated polymerization of N-carboxy anhydrides, ∈-caprolatine, and also norborene derivatives. In another approach, selective UV radiation of SAMS of photoiniators can be applied, using a mask or patterned photoresist, to create surface patterns. Improved nanopatterning is said to be achievable by the use of chemical lithography in which electron beams are used to drive reactions with SAMs in specific patterns. Chemical lithography should be able to give structures over a broader length scale than methods based on scanning probe microscopy and microcontact printing.

Other principles for nanofabrication of gecko-like adhesives are disclosed in U.S. patent application Ser. No. 10/197, 763, filed Jul. 18, 2002 by Fearing et al. and in U.S. patent application Ser. No. 10/039,574, filed Jan. 2, 2002 by Autumn et al., previously incorporated by reference.

Method of Assembly

Attachment of the gecko-like fastening material to a diaper or other absorbent article can be done according to any known method in the art, such as the methods disclosed in U.S. Pat. No. 5,399,219, "Method for Making a Fastening System for a Dynamic Fitting Diaper," issued Mar. 21, 1995 to Roessler et al., herein incorporated by reference. In the methods of U.S. Pat. No. 5,399,219, a plurality of fastener assemblies is formed by first providing a substantially continuous web of substrate material along a selected, longitudinal direction. The substrate web has a major facing surface thereof, and has first and second side edge regions. The fastening means, which is the gecko-like adhesive material for purposes of the present invention, is attached to or formed on the major facing surface of the substrate web. In some examples, a first web of stiffening material may be attached to the substrate web at a location which is proximate the first side edge region of the substrate web, and a second web of stiffening material is attached to the substrate at a location which is proximate the second side edge region of the substrate web. In other examples, no stiffening material is added. A medial region of the substrate web is separated along an undulating serpentine separation line to provide at least first and second fastener tab subassemblies. In particular configurations, either or both webs of side panel material are constructed of an elastomeric material which is stretchable at least along a cross-deckle direction of the method.

A further process aspect of U.S. Pat. No. 5,399,219, as adapted for the present invention, comprises a method for forming a plurality of adhesive fastener assemblies, which includes the step of providing a substantially continuous web of substrate material along a selected, longitudinal machine-direction. The substrate web has a laterally extending cross-direction which is substantially perpendicular to said machine-direction, and has laterally opposed, longitudinally extending side edge regions. A component of a primary fastening means (the gecko-like fastening material) is provided on a major facing surface of the substrate web. In some embodiments, a first longitudinally extending web of stiffening material is attached to the substrate web at a location which is proximate a first of the substrate side edge regions, and a second longitudinally extending web of stiffening material is attached to the substrate web at a location which is proximate a second of the substrate side edge regions. The substrate web is separated along a longitudinally extending medial region thereof with a substantially regularly undulating serpentine separation line to provide for an opposed pair of fastener tab subassemblies. At least one of the fastener tab subassemblies is divided along a plurality of division lines which extend substantially laterally across the at least one subassembly to provide a plurality of fastener tab components having an appointed factory bond region thereof. The factory bond regions of a plurality of said fastener tab components are connected to at least one longitudinally extending side edge region of a substantially continuous web of elastomerically stretchable material which is elastomerically stretchable at least along the cross-direction. The elastomerically stretchable web is severed along a plurality of severance lines which extend substantially laterally across the stretchable web to provide for a plurality of composite panel-and-fastener components.

Still another process aspect of the invention provides a method for forming an article having stretch panel fasteners, which includes the step of providing a first, substantially continuous web of elastomerically stretchable material along a selected, longitudinal machine-direction. The material is elastomerically stretchable at least along a laterally extending cross-direction which is substantially perpendicular to the machine-direction. At least a second, substantially continuous web of the elastomerically stretchable material is provided along the machine-direction, and the second web of stretchable material is spaced from the first web of stretchable material by a selected distance along the cross direction. A substantially continuous web of substrate material is provided along the machine-direction at a location which is between the first and second webs of stretchable material. The substrate web has laterally opposed, longitudinally extending side edge regions thereof. A longitudinally extending lateral side edge region of the first web of stretchable material is attached to the first, side edge region of the substrate web to provide a first bonded region. A longitudinally extending lateral side edge region of the second web of stretchable material is attached to the second, side edge region of the substrate web to provide a second bonded region. A first longitudinally extending web of stiffening material is overlapped over the first bonded region and the first stiffening web is connected to the first web of stretchable material and to the substrate web. A second longitudinally extending web of stiffening material is overlapped over the second bonded region and the second stiffening web is connected to the second web of stretchable material and to the substrate web. The substrate web is separated along a longitudinally extending medial region thereof with a substantially regularly undulating serpentine separation line to provide an opposed pair of composite subassemblies. At least one subassembly is divided along a plurality of division lines which extend substantially laterally across the subassembly to provide a plurality of longitudinally paired, combined panel-and-fastener components.

The various process aspects of the present invention can advantageously provide an efficient technique for rapidly producing the taping system of the invention. In particular configurations, the method can be carried out in-line with the process for manufacturing the associated article that employs the tape fastening system with the gecko-like adhesive material, thereby helping to reduce costs.

Description of Representative Articles

Figure 5:
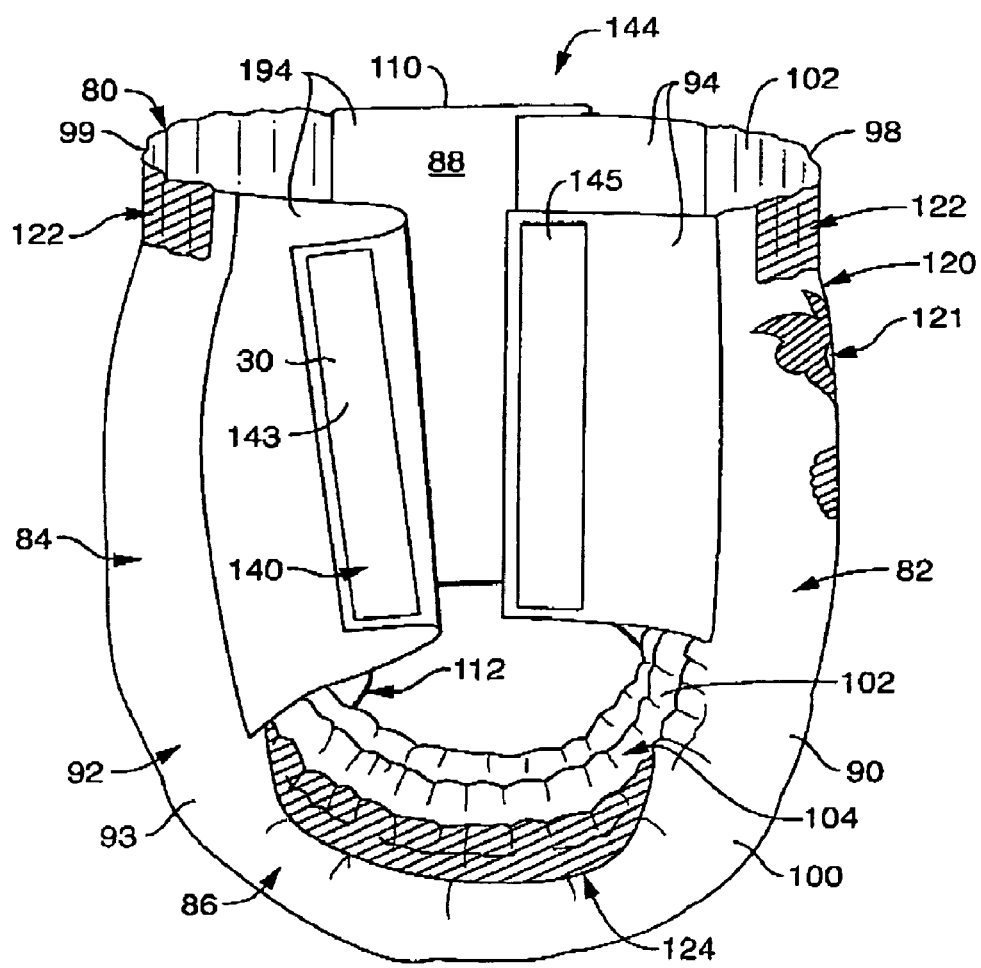
FIG. 5 is an absorbent article in the form of a training pant in a partially fastened mode.
Figure 6:
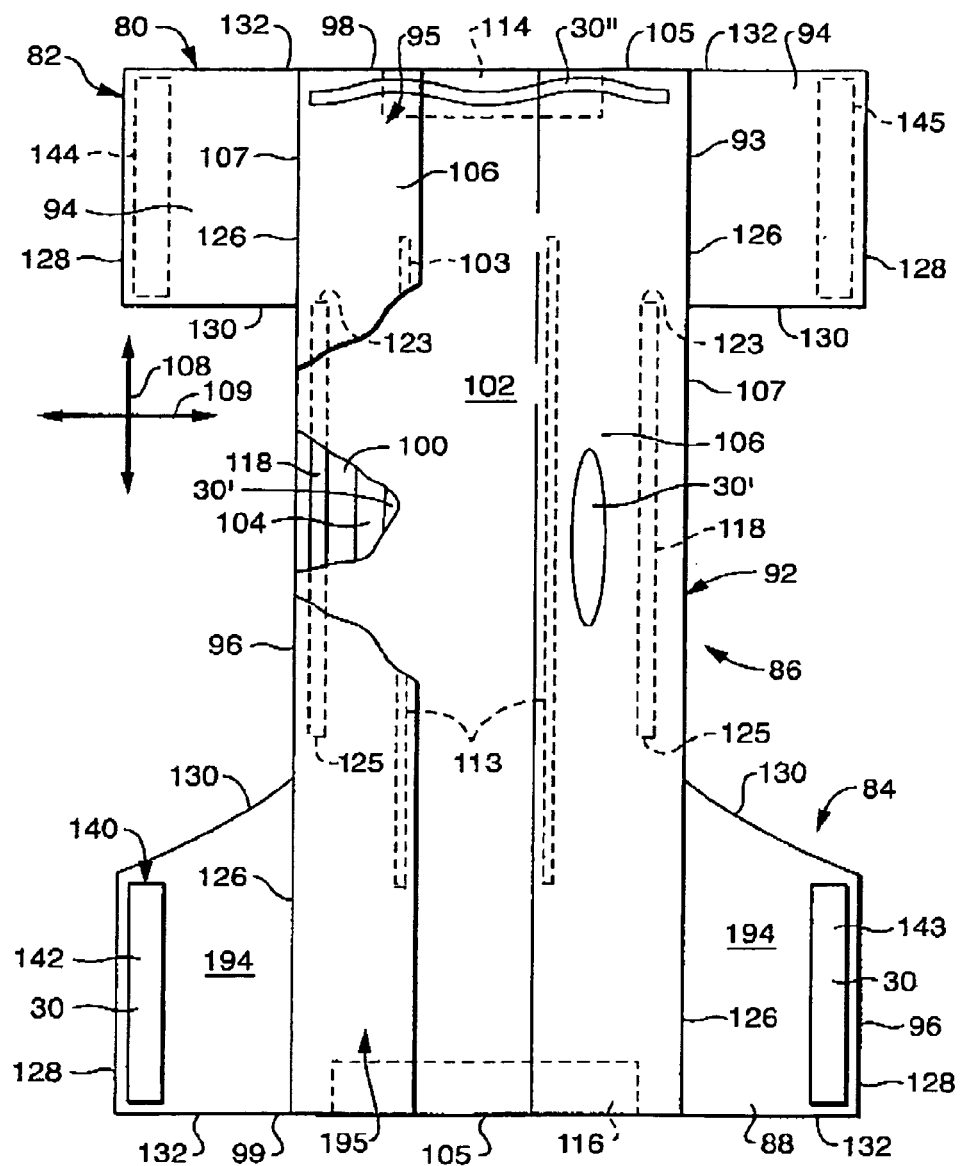
FIG. 6 is an absorbent article in the form of a training pant in an unfastened mode.
Figure 7:
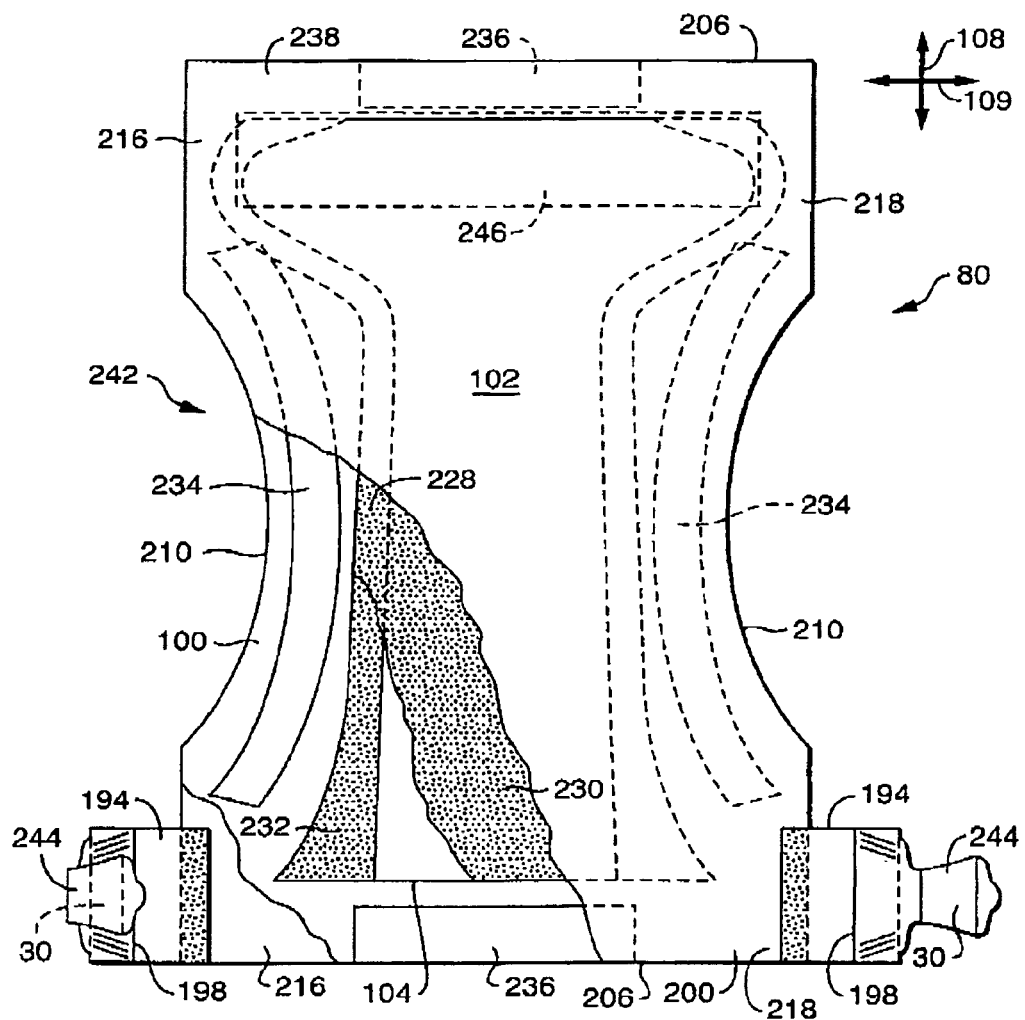
FIG. 7 is an absorbent article in the form of a disposable diaper.

In one example of the present invention, the materials and methods can be employed to produce a plurality of selected panel-and-fastener components for various articles, as illustrated in FIGS. 5 to 7.

As shown in FIGS. 5 and 6, a disposable absorbent article 80, here depicted as a training pant, can comprise the adhesive material 30 according to the present invention. The absorbent article 80 is related to the training pant of U.S. Pat. No. 6,562,167, "Methods for Making Garments with Fastening Components," issued May 13, 2003 to Coenen et al. It is illustrated in a partially fastened mode in FIG. 5 and in an unfastened mode in FIG. 6. The absorbent article 80 comprises an absorbent chassis 92 and a fastening system 140 having a strip of the adhesive material 30 of the present invention. The absorbent chassis 92 defines a front waist region 82, a back waist region 84, a crotch region 86 interconnecting the front and back waist regions, an inner surface 88 which is configured to contact the wearer, and an outer surface 90 opposite the inner surface which is configured to contact the wearer's clothing. The absorbent chassis 92 also defines a pair of transversely opposed side edges 96 and a pair of longitudinally opposed waist edges, which are designated front waist edge 98 and back waist edge 99. The front waist region 82 is contiguous with the front waist edge 98, and the back waist region 84 is contiguous with the back waist edge 99.

The illustrated absorbent chassis 92 comprises a composite structure 93 which can be rectangular or any other desired shape, a pair of transversely opposed front side panels 94, and a pair of transversely opposed back side panels 194. The composite structure 93 and side panels 94 and 194 may comprise two or more separate elements, as shown in FIG. 5, or may be integrally formed. Integrally formed side panels and composite structure would comprise at least some common materials, such as the bodyside liner, flap composite, outer cover, other materials and/or combinations thereof, and could define a one-piece elastic, stretchable, or nonstretchable pant, which may further comprise segments of gecko-like adhesive material (not shown) disposed on the outer surface thereof.

The absorbent article 80 and in particular the outer cover 100 may comprise one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product. Graphics depicting geckos or gecko feet or depicting the adhesive power of gecko feet (e.g., an image of gecko adhering to a flat surface) may be displayed on the article to convey its novel adhesive functionality.

The appearance-related components may be positioned on an absorbent article at selected locations, which can be carried out using the methods disclosed in U.S. Pat. No. 5,766,389 issued Jun. 16, 1998 to Brandon et al., which is incorporated herein by reference. The primary pictorial image may be positioned in the front waist region 82 along the longitudinal center line of the absorbent article 80.

The illustrated absorbent article 80 includes a fastening system 140 for refastenably securing the training pant about the waist of the wearer. The illustrated fastening system 140 includes first fastening components 142 and 143 that are adapted to refastenably connect to mating second fastening components 144 and 145. When the first fastening components 142 and 143 comprise gecko-like adhesive material 30, as shown, the second fastening components can comprise material joined to the front side panels 94 or may simply be the outer cover 100 itself or any existing functional component of the absorbent article 80, in which case the second fastening components may simply be regions of other materials onto which the first fastening components 142, 143 can be attached. Alternatively, the second fastening components may comprise materials particularly suited for attachment to gecko-like adhesive hairs, such as a textured hydrophobic web or smooth hydrophobic film of known compatibility with the materials of the adhesive material 30 (simple adhesive testing can be done to select a suitable material for the second fastening components). Alternatively, the second fastening components may also comprise regions of gecko-like adhesive material 30 (not shown). When gecko-like adhesive material 30 is not present or is not the sole adhesive element of the fastening system 140, hook and loop materials or conventional adhesives may also be present in selected regions of the fastening system 140. Suitable loop materials are available from Guilford Mills, Inc., Greensboro, N.C. U.S.A. under the trade designation No. 36549. Another suitable loop material can comprise a pattern un-bonded web as disclosed in U.S. Pat. No. 5,858,515 issued Jan. 12, 1999 to Stokes et al. Suitable hook material can be molded or extruded of nylon, polypropylene or another suitable material. Suitable single-sided hook materials for the fastening components 82-85 are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a unidirectional hook pattern and having a thickness of about 0.5 millimeters (20 mils); and Minnesota Mining & Manufacturing Co., St. Paul, Minn. U.S.A., including specific materials identified as CS-600.

With particular reference to FIG. 6, the first fastening components 142 and 143 are desirably although not necessarily disposed on the inner surface 88 of the absorbent article 80 in the back waist region 84. The first fastening components 142 and 143 are desirably positioned along the distal edges 128 of the back side panels 194, and abutting or adjacent to the waist end edge 132. In certain embodiments, for example, the first fastening components 142 and 143 can be located within about 2 centimeters, and more particularly within about 1 centimeter, of the distal edges 128, the waist end edges 132, and the leg end edges 130.

FIG. 7 depicts another example of an absorbent article 80, in this case a disposable diaper in which at least one strip of adhesive material 30 is used. Apart from the new use of gecko-like adhesive material 30, much of the design of the chassis and other components of the absorbent article 80 is disclosed by Roessler et al. in U.S. Pat. No. 5,399,219, "Method for Making a Fastening System for a Dynamic Fitting Diaper," issued Mar. 21, 1995, herein incorporated by reference in its entirety.

The article comprises a fastening means, such as a fastening assembly 244 that is connected to each of the stress beam sections 198 and is arranged to extend laterally from each of the side panels 194 for securing the waistband sections of the article about a wearer during the use of the article. In various embodiments of the invention, a fastening assembly 244 can be located at either or both of lateral end regions 216 and 218 of either or both of waistbands 238 and 240, respectively. The representatively shown embodiment has the fasteners located at the terminal side edges of rear waistband 240. The fastening assembly 244 can be bonded to the absorbent article 80 by any known means such as by ultrasonically welded bonds, thermal welds, adhesives, and the like, and one or more layers of additional material serving as tab substrates or bonding means, which may also enhance strength, stretching properties, or other features.

The fastening assembly 244 employs at least one section of adhesive material 30 with gecko-like functionality. The adhesive material 30 may be provided to the user in a protected form, such as covered within a folded fastening assembly 245, such that upon unfolding the fastening assembly 244 is opened to expose the adhesive material 30 for joining to the landing zone patch 246 or other portions of the absorbent article 80 (e.g., other portions of the outer cover 100).

Alternatively, because the adhesive material 30 may be more flexible than conventional mechanical fastening means and can be made to be integral with the outer cover 100 or with the side panels 194 (i.e., the substrate of the adhesive material 30 can be the same material as the outer cover 100 or side panels 194), a simplified design can be used (not shown) in which the side panels 194 and fastening assemblies 244 are substantially extensions of the outer cover 100 material or joined to the outer cover 100 material with a single seam or bond.

In one example, the adhesive material 30 comprises an elastomeric substrate (not shown) or is joined to an elastomeric side panel, such that the fastening assembly 244 can be stretched during attachment and detachment to somewhat imitate the peeling of setae from an attached surface as a gecko curls its toes when lifting a foot away from a surface. The adhesive hairs (not shown) can be positioned or angled for good attachment when a stretched side panel is relaxed after being put into place, and for good detachment when the side panel is stretched again and lifted. In one example, all or a portion of the adhesive hairs have an angle of inclination such that they lean toward the longitudinal centerline of the article (e.g., the tops of the adhesive hairs are generally slightly close to the longitudinal centerline than the bases of the respective adhesive hairs) when the absorbent article 80 is not attached, as in FIG. 7.

To provide a refastenable adhesive taping system, the absorbent article 80 may include a supplemental landing zone patch 246, which provides a target zone for receiving an attachment of fastener assembly 244 thereon. In the illustrated example of the invention, landing zone patch 246 is positioned on the outward surface of the outer cover 100 and is located on the second, front waistband portion 238 of the absorbent article 80. The landing zone patch 246 is constructed of a suitable material, such as polypropylene, polyester, or the like, and is configured and arranged to accept a secure adhesion of fastener assemblies 244. In addition, the landing zone patch 246 and the fastener assemblies 244 are cooperatively constructed and arranged to provide a releasable adhesion which allows the fastener assemblies 244 to be removed from the landing zone patch 246 for repositioning and re-adhesion without tearing or excessively deforming the material of the outer cover 100. For example, a suitable tape landing zone construction is described in U.S. Pat. No. 4,753,649 issued to Pazdernik, the disclosure of which is hereby incorporated by reference to the extent that it is consistent herewith.

In various examples of the invention, a fastener assembly 244 can be located at either or both of lateral end regions 216 and 218 of either or both of waistbands 238 and 240, respectively. The representatively shown example has the fasteners located at the terminal side edges of rear waistband 240. Another location suitable for further placement of adhesive material 30 of the present invention is over leg cuffs (not shown) or other cuffs, including on the bodyside liner 102 substantially over the leg elastic members 234 to join the absorbent article 80 to the body of the wearer for improved gasketing. The adhesive material 30 of the present invention may also be used to join the absorbent article 80 to other external items such as printed webs (not shown) with graphics that can be attached and removed from the outer cover 100 to provide customizable or removable graphics. Other components that could be attached to the absorbent article 80 with adhesive material 30 means could include biosensor components and the like.

In particular aspects of the invention, each of the side panels 194 may be formed from a separate piece of material, which is then suitably assembled and attached to the selected front and/or rear waistband portion of the absorbent article 80. In the illustrated embodiments of the invention, for example, side panels 194 are attached to the rear waistband portion of the outer cover 100, and may be operably attached to either or both of the outer cover 100 and bodyside liner 102 components of the article. The side panels extend laterally to form a pair of opposed waist-flap sections of the absorbent article 80, and are attached with suitable connecting means, such as adhesive bonding, thermal bonding, ultrasonic bonding, clips, staples, sewing or the like, or may be attached with removable fastening means (not shown) such as gecko-like adhesive material.

The adhesive material 30 may also be used in sanitary napkins, such as those disclosed in U.S. Pat. No. 5,681,303, "Sanitary Napkins Having Flaps and Stress Relief Means," issued Oct. 28, 1997," to Mills et al., herein incorporated by reference to the extent it is consistent herewith. Particular attention is called to FIGS. 2, 3, and 4 of U.S. Pat. No. 5,681,303, in which central pad adhesives or flap adhesives or both can be replaced with gecko-like adhesive material 30 to provide improved attachment to undergarments. Protective release paper or film may also be provided, if desired, to protect the adhesive material 30 when not in use. Release liners that also serve as an individual package for a sanitary napkin are described in U.S. Pat. No. 4,556,146 issued to Swanson, et al. and in PCT Publication No. WO 91/18574, published Dec. 12, 1991.

Another configuration of feminine care products which may benefit from the use of gecko-like adhesive materials is shown in U.S. Pat. No. 4,917,697, issued Apr. 17, 1990 to Osborn, III et al. The adaptation of gecko-like adhesive technology to such an article is illustrated in FIG. 8.

Figure 8:
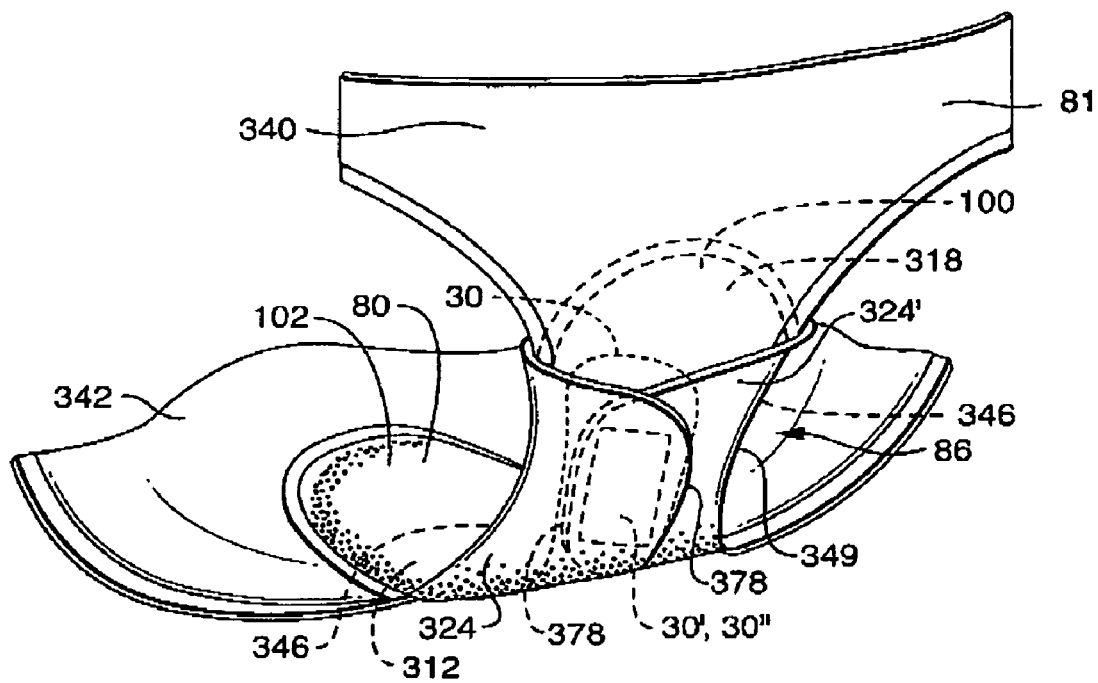
FIG. 8 is an absorbent article in the form of a feminine care product.

The absorbent article 80 (here a sanitary napkin) is utilized by removing any release liners (if present) and thereafter placing the absorbent article 80 in a panty 81 as shown in FIG. 8. The center of central absorbent pad 312, which lies between the outer cover 100 and the bodyside liner 102 of the absorbent article 80, is placed in crotch portion 86 of the panty 81 with one end of central absorbent pad 312 extending towards the front section 340 of the panty and the other end towards the back section 342 and with the outer cover 100 in contact with the inner surface of center crotch portion 86 of the panty. A central section of adhesive material 30 maintains the central absorbent pad 312 in position. The distal portions of flaps 324 and 324' are folded around, respectively, side edges 346 and 346'. Patches of gecko-like adhesive material 30', 30" serve as flap fasteners to secure flaps 324 and 324' in such position. thus, flaps 324 and 324' are each folded over themselves with a portion of the panty, including side edges 346 and 346', interposed therebetween. The flaps are folded over a fold line 349 defined by the edge of the panty 81 in the crotch region 86. As shown, the central section of adhesive material 30 is disposed between the outer cover 100 of the absorbent article 80 beneath the central absorbent pad 213 and the bodyside surface of the panty 81, while the patch of adhesive material 30', 30" on the flaps 324, 324' are the garment side of the panty 81, with one patch of adhesive material 30' being against the panty 81 itself, joining it to a flap 324', and the other patch of adhesive material 30" joining one flap 324 to the other flap 324'. The adhesive material 30', 30" may extend up to or near the distal edges 278, 278' of the flaps, if desired.

Numerous other sanitary napkin embodiments having flaps are available and are disclosed in the literature. For example, sanitary napkins having flaps are disclosed in U.S. Pat. No. 4,687,478 entitled "Shaped Sanitary Napkin With Flaps", which patent issued to van Tilburg on Aug. 18, 1987, U.S. Pat. No. 4,608,047, entitled "Sanitary Napkin Attachment Means", which patent issued to Mattingly on Aug. 26, 1986, U.S. Pat. No. 4,589,876, entitled "Sanitary Napkin", which patent issued to Van Tilburg on May 20, 1986, U.S. Pat. No. 4,285,343, entitled "Sanitary Napkin", which patent issued to McNair on Aug. 25, 1981, U.S. Pat. No. 3,397,697, entitled "Disposable Sanitary Shield For Undergarments", which patent issued to Rickard on Aug. 20, 1968, and U.S. Pat. No. 2,787,241, entitled "Sanitary Napkin", which patent issued to Clark on Apr. 2, 1957.

Gecko-like adhesive material can also be used to attach flapless absorbent articles such as sanitary napkins and pantiliners to the undergarments. In such cases, pressure-sensitive adhesives or non-skid material usually applied to a side of the absorbent article can be replaced or supplemented with gecko-like adhesive material 30. Examples of flapless sanitary napkins and pantiliners are presented in U.S. Pat. No. 4,834,739, "External Feminine Protection Device with Skid-Resistant Coating for Holding the Device in Place," issued May 30, 1989 to Linker, III et al., and U.S. Pat. No. 5,011,480, "Absorbent Article Having a Nonwoven Frictional Surface for Holding the Article in Place and a Method of Use," issued Apr. 30, 1991 to Gossens et al.

Cleaning Articles

The adhesive materials of the present invention can also be used to improve the attachment of other disposable articles such as cleaning sheets for dusting devices, dry mops, and wet mops, including the SWIFFER® brand of cleaning articles of Procter and Gamble (Cincinnati, Ohio) such as SWIFFER® WetJet™ and related floor cleaning articles. Gecko-like materials can also be effective in attaching sponges, mop heads, and cleaning cloths to re-usable heads and handles.

Exemplary disposable cleaning sheets that can be combined with gecko-like adhesive materials are disclosed in U.S. Pat. No. 6,561,354, "Package of Novel Three Dimensional Structures Useful as Cleaning Sheets," issued May 13, 2003 to Fereshtehkhou et al.; WO 01/41622, "Non-Apertured Cleaning Sheets Having Non-Random Macroscopic Three-Dimensional Character," published Jun. 14, 2001; WO 03/00104, "Disposable Cleaning Sheets Comprising a Plurality of Protrusions for Removing Debris from Surfaces," published Jan. 3, 2003; WO 98/52458; "Three-Dimensional Structures Useful as Cleaning Sheets," published Nov. 26, 1998; and European Patent Application 923902-A2, "Cleaning Product and Production Process Therefor," published Jun. 23, 1999 by Abe et al.

Figure 9A:
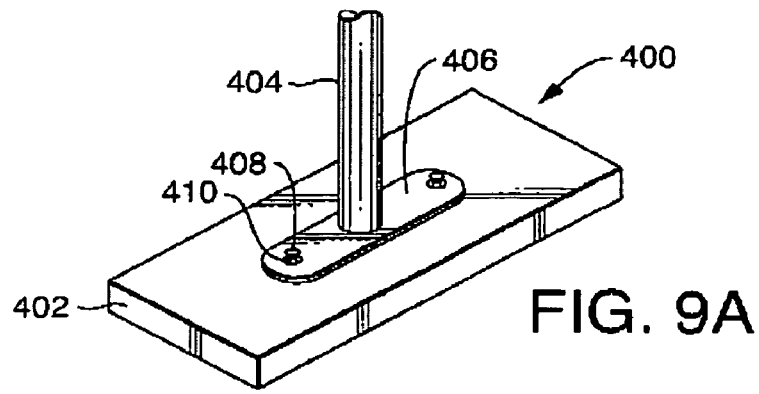
FIG. 9A depicts a mop head.
Figure 9B:
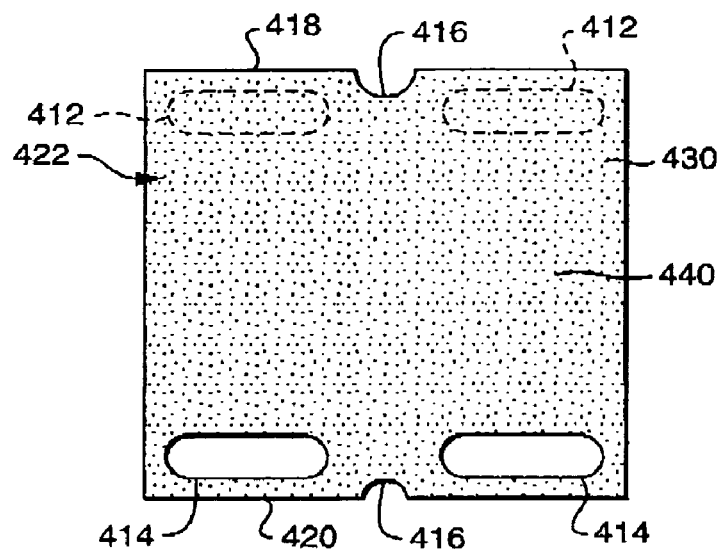
FIG. 9B depicts a mop head cover comprising gecko-like adhesive fasteners.
Figure 9C:
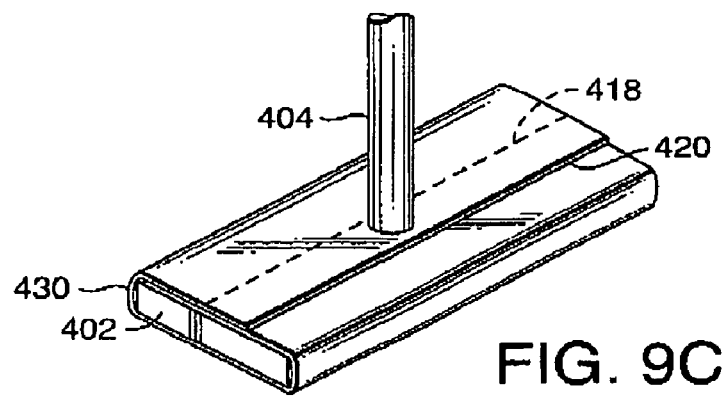
FIG. 9C depicts a mop head with a mop head cover attached with gecko-like adhesive fasteners.

One example of a cleaning article according the present invention is shown in FIGS. 9A-9C. Here a mop 400 includes a disposable mop head cover substrate 430 which fits mop head 402. Mop head cover substrate 430 has a first edge 418, second edge 420, and outward face 422. Substrate 420 can be made of a material or materials (ideally biodegradable), preferably suitable for performing a waste contamination removal function, and are described below and previously herein. As shown in FIG. 9C, mop head cover substrate 430 wraps around mop head 402 with first edge 418 overlapping second edge 420 and is held in place by the gecko-like fasteners 412, located near the first edge 418 on the opposite face of the substrate from the outer face 422, and which can join to patches of landing material 414, located near the second edge 420 on the outer face 422. The landing material may, if desired, be identical to the mop head substrate 430 (i.e., simply a part of the substrate 430 with no additional material added) or may comprise an additional layer of material secured to the substrate 430. Handle orifices 416 facilitate good fit around the handle 404 which is secured to the mop head 402 by a mounting plate 406 that is attached to the mop head 402 by screws, rivets, or other joining means. A waste contamination sensor 440, as described in U.S. Pat. No. 6,501,002, may be incorporated into or onto at least part of outward face 422 of substrate 430.

Figure 10A:
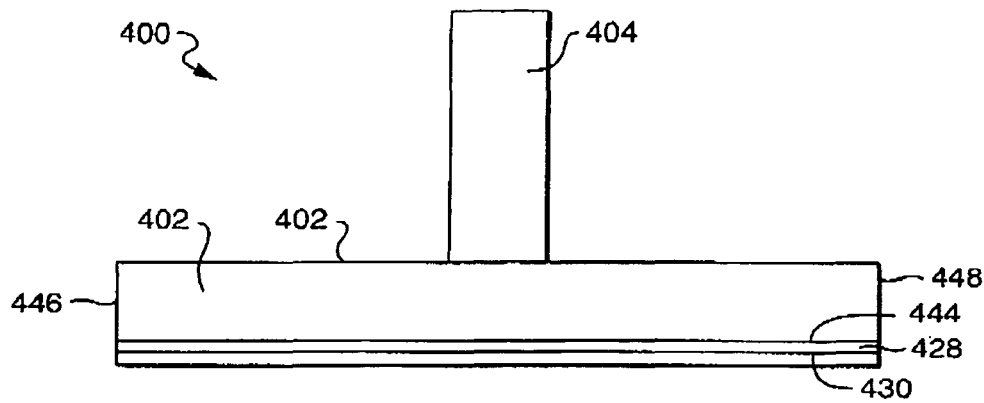
FIG. 10A is a side view of a mop head.
Figure 10B:
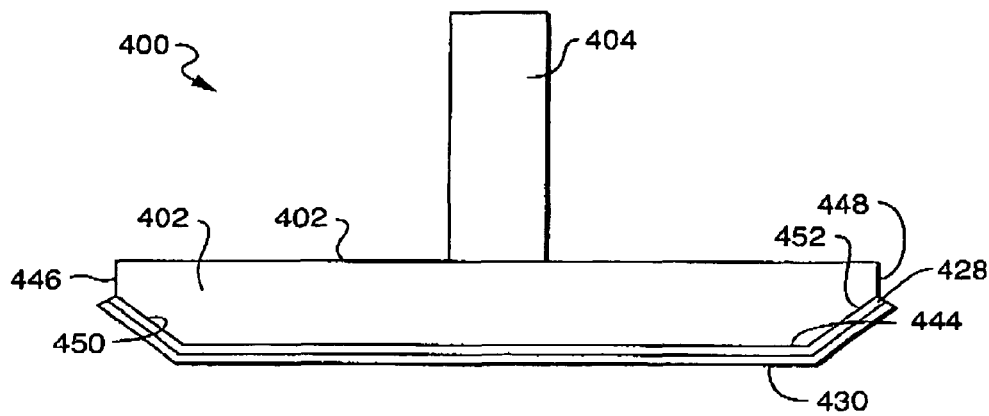
FIG. 10B is a side view of a mop head with a mop head cover attached with gecko-like adhesive fasteners.

FIGS. 10A and 10B depict another example of a mop 400 similar to that of FIG. 9, but in which the disposable mop head cover substrate 430 is joined to the mop head 402 by a gecko-like adhesive layer 428 such that the mop head cover substrate 430 no longer needs to wrap a major portion of the mop head 402, and in particular does not need to wrap the upper side 442 of the mop head 402 in order to be secured, for it is secured directly to the lower side 444 of the mop head 402. In FIG. 10A, the mop head cover substrate 430 is substantially coextensive with the lower side 444 of the mop head 402, with no material wrapping the front or rear edges 446, 448 or the upper side 442 of the mop head. The strong but removable attachment means provided by the gecko-like adhesive layer 428 allows the mop head cover substrate 430 to be used in wiping or mopping operations.

In FIG. 10B, the mop head 402 is provided with a beveled front region 450 and beveled read region 452 onto which the mop head cover substrate 430 is secured by means of the gecko-like adhesive layer 428. In this example, a portion of the front edge 446 and back edge 448 of the mop head 402 is wrapped by the mop head cover substrate 430, but there is no need for the material to wrap across the upper side 442 of the mop head 402, where the material would be wasted in terms of cleaning functionality. Thus, the system of FIGS. 10A and 10B provides for improved efficiency of the cleaning material used in the mop head cover substrate 430.

Example 1

Figure 11:
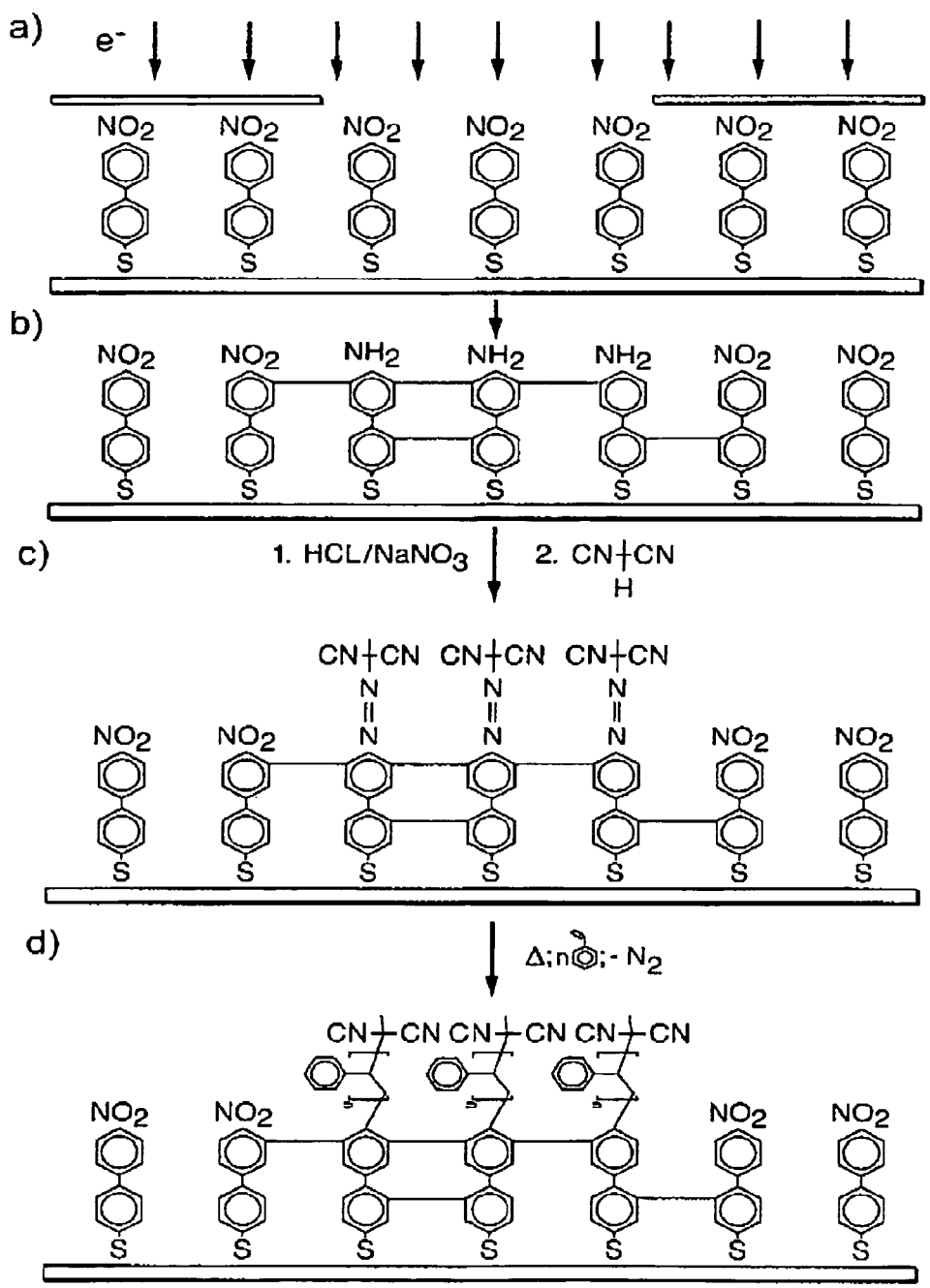
FIG. 11 is a surface-initiated polymerization for producing synthetic setae.

A hypothetical example of using surface-initiated polymerization for producing synthetic setae is illustrated in FIG. 11.

Example 2

Figure 12A:
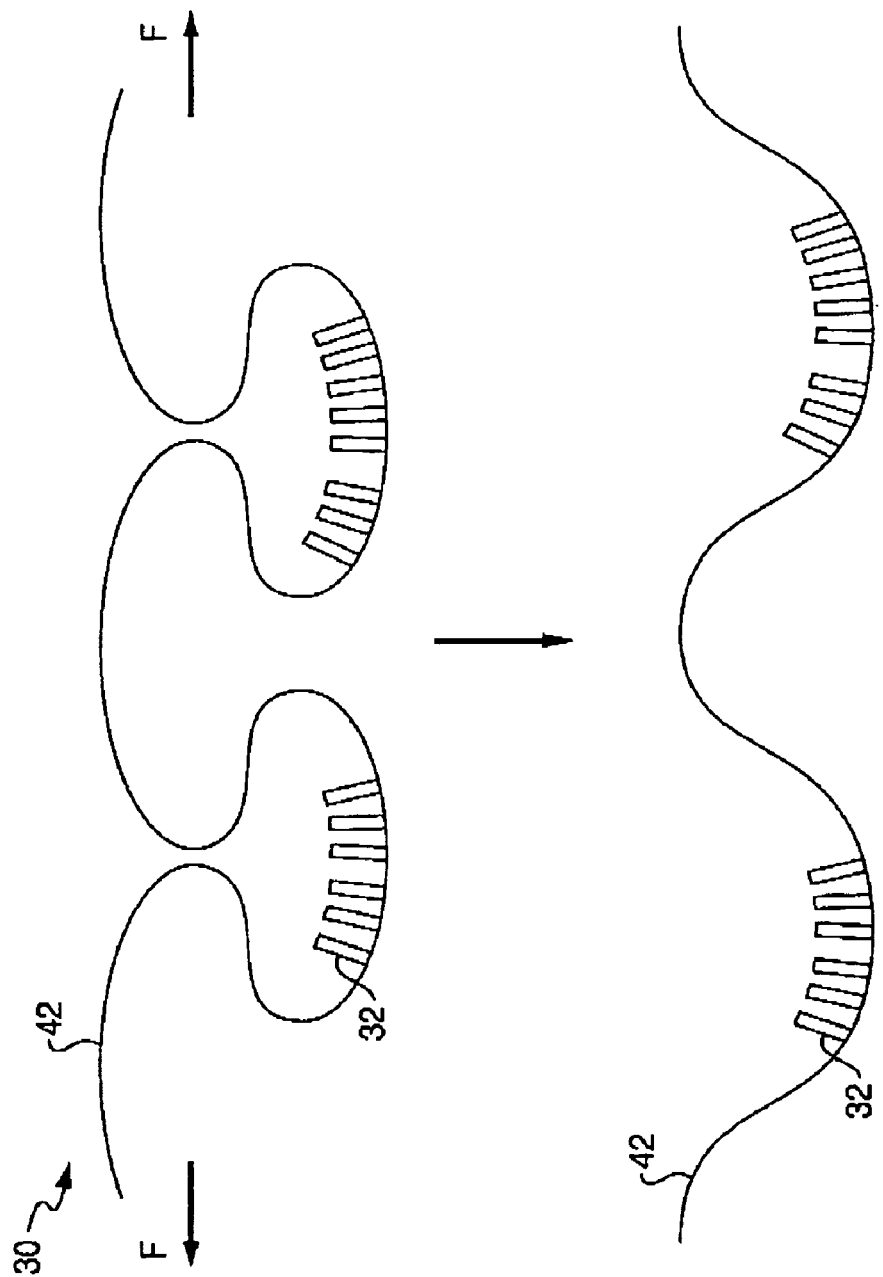
FIGS. 12A and 12B depict side views of the gecko-like adhesive material.

In yet another hypothetical example, the adhesive hairs are placed on a substrate in such a way that they are hidden inside the valleys or grooves on a substrate surface (FIG. 12A for a side view). These grooves are designed to protect the hairs from contaminants during the manufacturing process, e.g. the process of putting together an absorbent article. When in use, adhesive material is activated by applying a moderate stretch in the direction perpendicular to the direction of the grooves. That stretch opens up the grooves and makes the adhesive hairs available for interaction with the attachment surface (not shown).

Figure 12B:
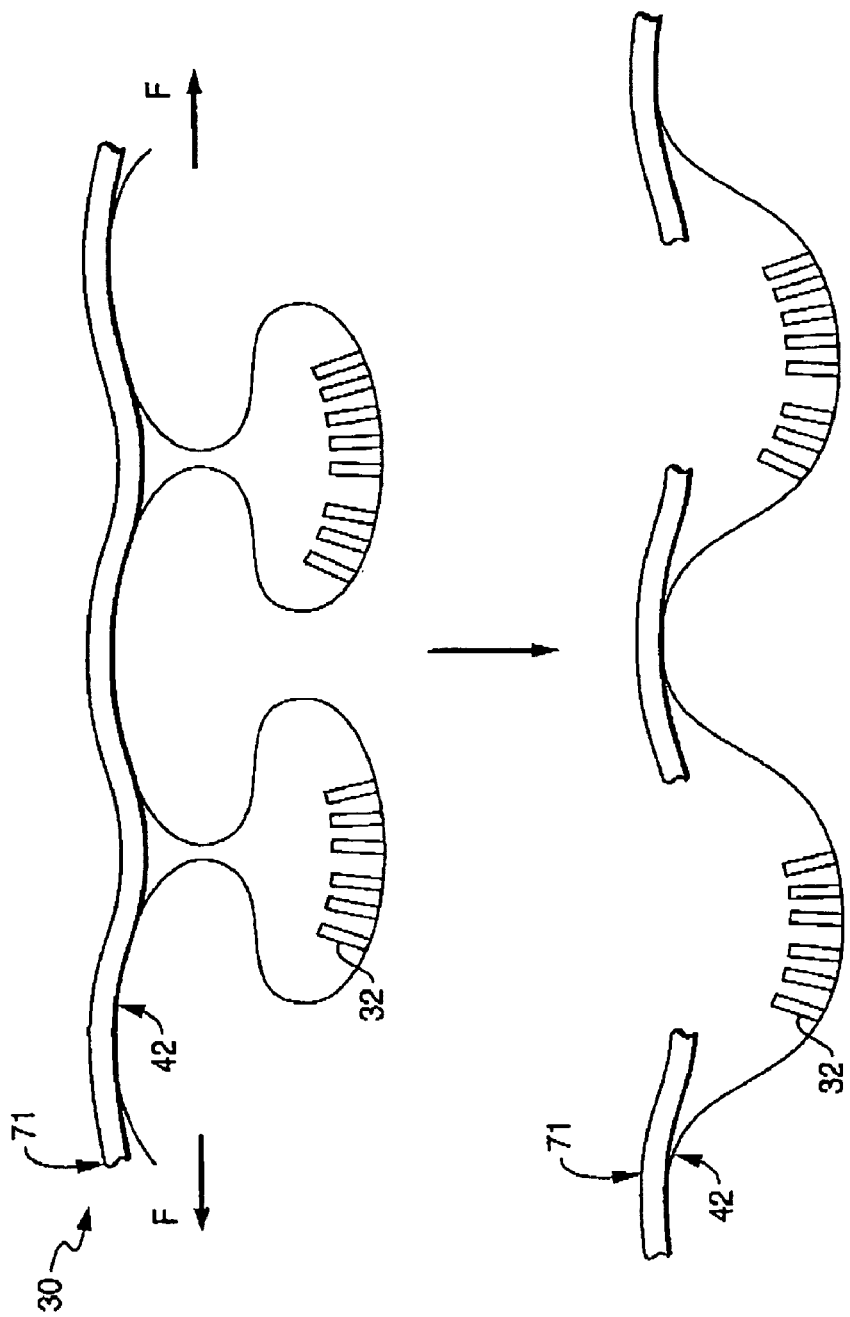

Yet another example is presented on FIG. 12B. In this example a substrate with the adhesive hairs/setae attached to it is laminated to a thin film 71 that provides additional protection for adhesive hairs/setae while not in use. In this example, the activation mechanism could be stretching of the substrate in the direction perpendicular to the grooves, which results in breaking of the protective film. This releases adhesive hairs and makes them available for the interaction with the attachment surface. Besides providing the benefit of contamination resistance, examples presented in FIG. 12A and FIG. 12B also have an advantage of not engaging with unwanted surfaces such as, for example, baby or caregiver clothes, etc.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description shall be interpreted as illustrative and not in a limiting sense.

What is claimed is:

1. A disposable absorbent article comprising a nanofabricated attachment means comprising adhesive hairs disposed on a flexible substrate, wherein said hairs are effective to adhesively engage an opposing surface comprising a polymeric film or a fibrous web, wherein the attachment means has a packing density of at least 500 hairs per square millimeter, wherein said hairs do not consist of a spatula or protrusion positioned at a terminal end of the hairs, and wherein said hairs have an average diameter of about 50 microns or less and an average height-to-diameter ratio of about 3 or greater.

2. A disposable absorbent article comprising a nanofabricated attachment means comprising adhesive hairs disposed on a flexible substrate, wherein the attachment means has a packing density of at least 500 hairs per square millimeter, wherein said hairs do not consist of a spatula or protrusion positioned at a terminal end of the hairs, and wherein said hairs are effective to adhesively engage an opposing surface comprising a polymeric film or fibrous web with an average adhesive force of 10 nanoNewtons or greater per hair.

3. A disposable absorbent article comprising a gecko-like adhesive fastener including a flexible substrate, a plurality of adhesive hairs rising from said substrate, said hairs each having a base section, a midsection, a top section, a height of about 0.5 microns to about 8 millimeters, and a diameter of about 0.05 microns to about 50 microns, and wherein said hairs do not consist of a spatula or protrusion positioned at a terminal end of the top section.

4. The article of claim 3 wherein said hairs have a height of about 2 microns to about 1000 microns.

5. The article of claim 3 wherein said hairs have a diameter of about 0.05 microns to about 10 microns.

6. The article of claim 3 wherein said hairs are spaced apart by a first distance of about 1 micron to about 1000 microns.

7. The article of claim 3 wherein said hairs are spaced apart by a second distance of about 1 micron to about 1000 microns.

8. The article of claim 3 wherein the ratio of a first distance between said hairs to the diameter of said hairs is about 3 to about 100.

9. The article of claim 3 wherein the ratio of a second distance between said hairs to the diameter of said hairs is about 3 to about 100.

10. The article of claim 3 wherein the ratio of the height of said hairs to the diameter of said hairs is about 2 to about 1000.

11. The article of claim 3 wherein at least one of said hairs is perpendicular to the plane of said substrate.

12. The article of claim 3 wherein at least one of said hairs is oriented at an angle between 0° and 90° to the plane of said substrate.

13. The article of claim 3 wherein at least one of said hairs is axisymmetric.

14. The article of claim 3 wherein at least one of said hairs is hollow.

15. The article of claim 3 wherein said at least one hair comprises hollow materials, microspheres, carbon nanotubes, zeolites, or combinations thereof.

16. The article of claim 3 wherein said hairs comprise molecules with hollow chambers.

17. The article of claim 16 wherein said molecules are cyclodextrins, crown ethers, polyhedral oligomeric silsequioxanes, or combinations thereof.

18. The article of claim 3 wherein said substrate is apertured.

19. The article of claim 3 wherein said substrate is a liquid impervious web.

20. The article of claim 3 wherein the thickness of said substrate comprises a repeating pattern of thickness variations.

21. The article of claim 3 wherein said substrate is creped, embossed, apertured, coated, or combinations thereof.

22. The article of claim 21 wherein said coating is on at least one side of said substrate.

23. The article of claim 21 wherein said coating is hydrophobic.

24. The article of claim 21 wherein said coating is hydrophilic.

25. The article of claim 21 wherein said coating is a metal oxide.

26. The article of claim 21 wherein said metal oxide is titanium dioxide treated with a UV absorbing material that is thermally treated.

27. The article of claim 3 wherein said substrate comprises regions of elastic material.

28. The article of claim 3 wherein said substrate is substantially elastic and homogeneous.

29. The article of claim 3 wherein said substrate contains discrete elastic regions separated by less elastic regions.

30. The article of claim 3 wherein said substrate contains discrete elastic regions separated by inelastic regions.

31. The article of claim 3 wherein said fastener is stretchable.

32. The article of claim 3 wherein said fastener comprises elastic regions.

33. The article of claim 3 wherein an attachment surface of said fastener is elastic, inelastic, or combination thereof.

34. The article of claim 3 wherein said fastener is adapted for fastening said article to itself.

35. The article of claim 3 wherein said fastener is adapted for fastening said article to another object.

36. The article of claim 3 wherein said fastener is adapted for joining two or more components of said article.

37. The article of claim 3 wherein said fastener comprises part of a side seam of said article.

38. The article of claim 3 wherein said fastener comprises a three-dimensional topography characterized by a series of peaks and valleys.

39. The article of claim 38 wherein said peaks and valleys alternate in a first direction.

40. The article of claim 38 wherein groups of hairs are selectively disposed on said peaks of said substrate, said valleys of said substrate, or combination thereof.

41. The article of claim 3 wherein said hairs are protected from contamination with other materials until pressed into contact with an opposing surface.

42. The article of claim 3 wherein said hairs are protected with a removable cover.

43. The article of claim 3 wherein said fastener comprises substantially hair free regions between groups of hair.

44. The article of claim 3 wherein said hairs are disposed substantially uniformly along the fastener.

45. The article of claim 3 wherein said hairs are disposed substantially randomly along the fastener.

* * * * *